United States Patent [19]

Nelson et al.

[11] Patent Number: 5,391,188
[45] Date of Patent: Feb. 21, 1995

[54] LOW COST IMPLANTABLE MEDICAL DEVICE

[75] Inventors: Gary E. Nelson, Balsam Lake, Wis.; David L. Thompson, Fridley, Minn.

[73] Assignee: Medtronic, Inc., Minneapolis, Minn.

[21] Appl. No.: 78,382

[22] Filed: Jun. 17, 1993

Related U.S. Application Data

[63] Continuation-in-part of Ser. No. 44,433, Apr. 5, 1993, abandoned, which is a continuation-in-part of Ser. No. 877,639, May 1, 1992, Pat. No. 5,292,342.

[51] Int. Cl.$^6$ .............................................. A61N 1/00
[52] U.S. Cl. ........................................... 607/9; 607/32
[58] Field of Search ...................... 607/9, 30, 32, 60

[56] References Cited

U.S. PATENT DOCUMENTS

| | | | |
|---|---|---|---|
| 4,273,132 | 6/1981 | Hartlaub | 128/419 |
| 4,476,868 | 10/1984 | Thompson | 128/419 |
| 4,651,740 | 3/1987 | Schroeppel | 607/030 |
| 5,312,446 | 5/1994 | Holschbach . | |

FOREIGN PATENT DOCUMENTS 30132 6/1981 European Pat. Off. ............ 607/030

OTHER PUBLICATIONS

Frank Goodenough, "IC Holds 16 Seconds of Audio Without Power", Electronic Design, Jan. 31, 1991, pp. 39–44.

Information Storage Devices, Inc. ISA 1016 Series Preliminary Specifications, Jan., 1991, 9 pages.

Bill Arnold, "Here comes analog memory", EDN News Edition, Feb. 7, 1991, vol. 36, No. 3A, pp. 1 and 38.

*Primary Examiner*—William E. Kamm
*Assistant Examiner*—Marianne Parker
*Attorney, Agent, or Firm*—Harold R. Patton

[57] ABSTRACT

A low cost, limited-function implantable medical device. The device's synchronous circuits are driven by an ultra-slow master clock signal produced without utilization of a crystal oscillator. The device is non-invasively programmable by means of an externally applied programming magnet, which is detected by a solid state magnetic sensor (MAGFET) circuit in the implanted device. The MAGFET circuit is capable of discriminating between two polarity orientations of the programming magnet, so that one polarity is associated with increasing programmable parameters and the opposite polarity is associated with decreasing programmable parameters. Upon initial placement and detection of the programming magnet, the disclosed device performs a threshold margin test comprising three asynchronous stimulating pulses at the current pulse width and pulse amplitude settings.

24 Claims, 17 Drawing Sheets

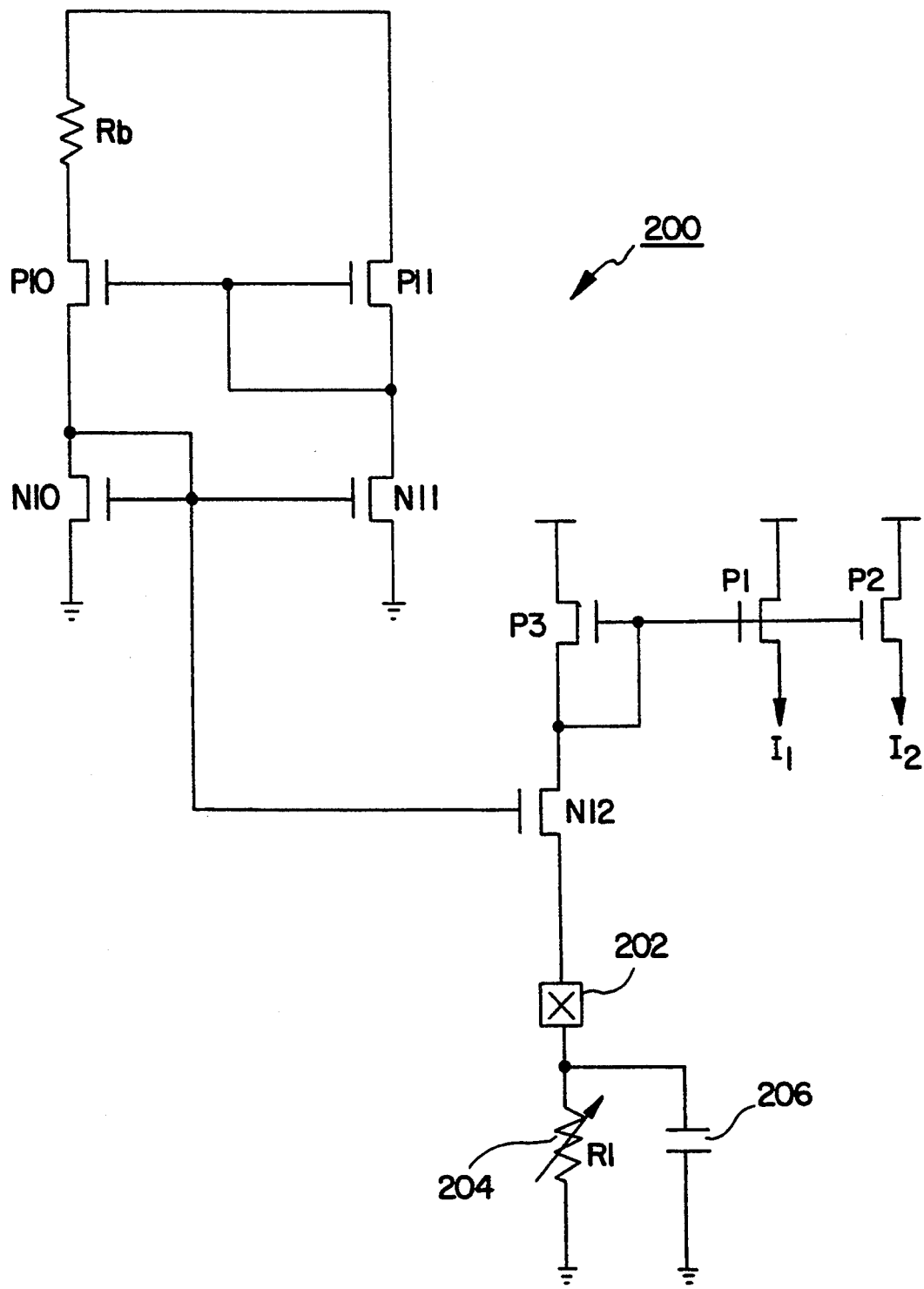
F I G. 11

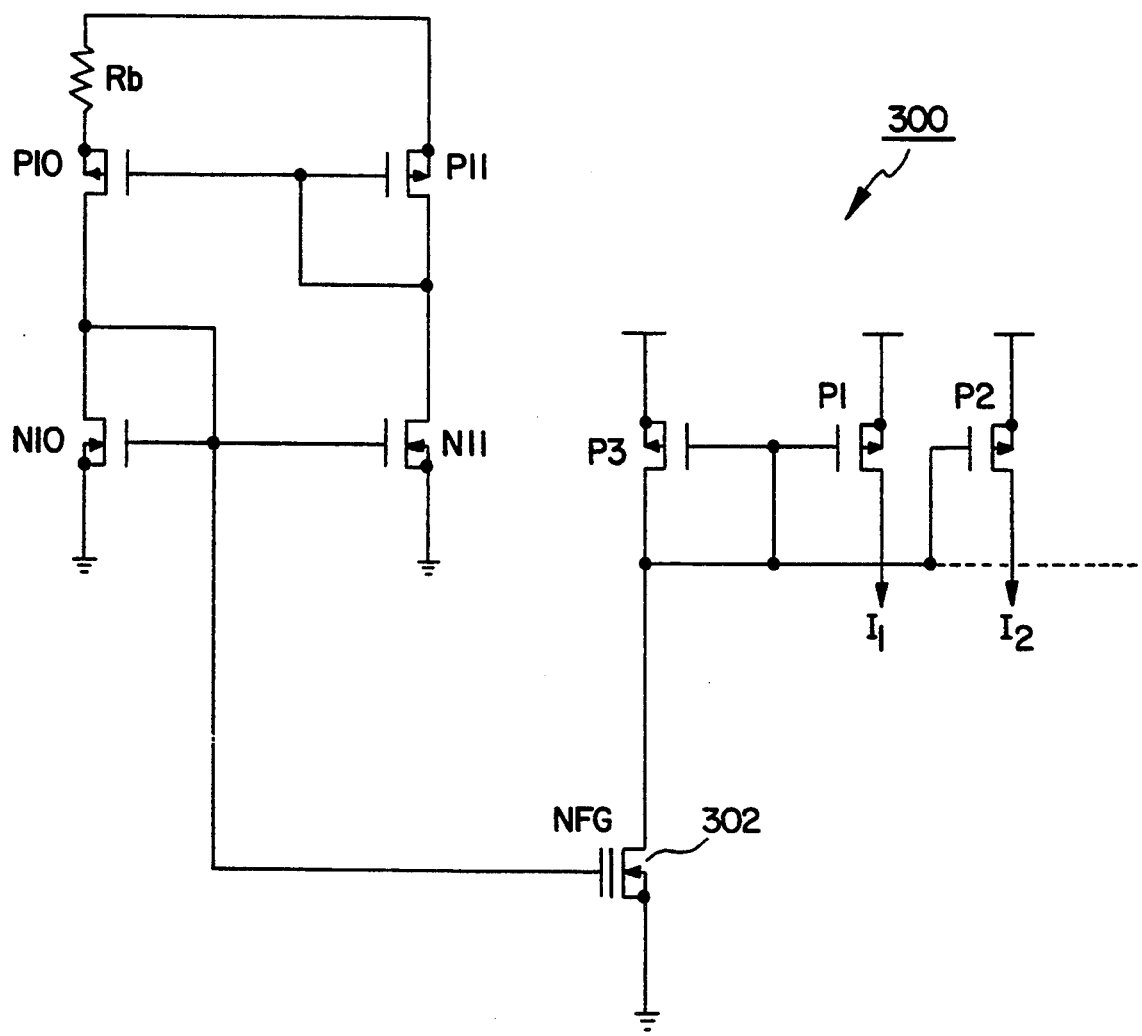
F I G. 12

LOW COST IMPLANTABLE MEDICAL DEVICE

CROSS REFERENCE TO CO-PENDING APPLICATION

This application is a continuation-in-part of commonly assigned U.S. patent application Ser. No. 08/044,433, filed Apr. 5, 1993, entitled "Low Cost Implantable Medical Device", now abandoned, and which is a continuation-in-part of commonly assigned U.S. Pat. No. 5,292,842, issued Mar. 8, 1994, filed May 1, 1992, now entitled "Low Cost Implantable Medical Device" Ser. No. 877,639.

FIELD OF THE INVENTION

This invention relates to the field of implantable medical devices, and more particularly relates to a low cost implantable cardiac pacemaker configuration.

BACKGROUND OF THE INVENTION

The field of implantable medical devices, including cardiac pacemakers, cardioverters, defibrillators, drug-administering devices, neural stimulators, and the like, has seen considerable advancement over the last several decades. This progress in medical device technology stems not only from advances in medical knowledge, but also to a great extent from recent improvements in the areas of electronics and semiconductors. By taking advantage of the latest technological improvements, manufacturers have been able to increase the overall effectiveness and usefulness of medical devices by increasing their functional capability, sophistication, and complexity.

Early implantable pacemakers, which delivered cardiac stimulating pulses at a fixed rate without inhibition, may seem primitive in comparison to today's state-of-the-art multifunctional pacemakers. Today, pacemakers are available which are programmable into one of various operational modes, from simple single-chamber asynchronous pacing to dual-chamber, synchronous, demand pacing. Many modern pacemakers are capable of automatically adjusting their pacing rates in response to a patient's intrinsic electrical cardiac activity and/or the level of a patient's metabolic demand for oxygen. Most state-of-the-art pacemakers are programmable or multi-programmable, such as with an external programmer which communicates with the implanted device via radio-frequency telemetry. A pacemaker may be programmable with respect to numerous parameters, including pacing mode (DDD, VDD, AOO, etc. . . . ), pacing rate, stimulating pulse width, refractory period, sense amplifier sensitivity, rate-responsiveness to measured physiological parameters, and so on.

Since implantable medical devices are typically implanted subcutaneously and may be implanted in a patient for many years, it has always been an objective in the design of implantable devices that they be as small and lightweight as possible. Often, there is a trade-off between size and functionality of a device. Increasing the functionality of an implanted device can involve increasing the size, weight, and power consumption of the circuitry and/or other functional components required to realize increased functional capability. Power consumption is an important consideration because increased power consumption will be associated with either an increase in battery size and weight, or a decrease in the device's operational life expectancy.

Pacemaker designers and manufacturers have had considerable success in balancing such considerations as pacemaker functionality, sophistication and complexity with considerations of size, weight, and power consumption. In many cases, however, the balancing of these factors comes at considerable economic expense. That is, pacemakers which are fully-featured and highly sophisticated, and at the same time small, light-weight, and long-lived, have become increasingly expensive to design, manufacture, and sell. State-of-the-art pacemakers in some cases cost the consumer three to four thousand dollars or more.

The problems of high implantable medical device costs are further aggravated by the large expense allocable to research and development for these state-of-the-art devices, as well as by the expense associated with extensive clinical investigation and regulatory approval procedures required in most countries.

A fully-featured and highly sophisticated state-of-the-art pacemaker (e.g., a multiprogrammable, dual-chamber, rate-responsive or DDDR pacemaker) may be appropriate for certain pacemaker candidates, such as those with the most serious or complicated cardiac disorders. However, there are also those pacemaker candidates with cardiac conditions for which only a simple pacemaker therapy (e.g., single chamber demand pacing) is indicated. In some instances, a physician can minimize the costs for a pacemaker patient by implanting a small, limited-function pacemaker when a more extensive pacemaker therapy would be unnecessary. That is, a physician can select from among many commercially available pacemakers covering a wide range of sophistication and functionality, and can select a pacemaker whose functionality most closely meets the needs of the pacemaker candidate.

It is believed by the inventors, therefore, that there remains an ongoing need for limited function, low cost implantable pacemakers to meet the needs of pacemaker candidates whose conditions do not require all of the features of more sophisticated and complex pacemakers.

It is also believed that the present invention is applicable to other types of implantable medical devices besides pacemakers, in cases where a limited-functionality version of a given medical device, rather than a more expensive and complex version, may provide appropriate and effective treatment for some candidates.

According to the present invention, several of the sub-systems in an implantable device are down-scaled and/or simplified in order to reduce associated design, manufacturing, and production costs. These subsystems include the master timing oscillator, the programming system, and internal timing systems.

In prior pacemakers, it has been common to measure certain time intervals, such as pacing periods, A-V delay periods, refractory and blanking periods, and so on, by means of a crystal oscillator. Typically, the crystal oscillator produces a clock signal having relatively high frequency, for example 32,768-Hz. This base frequency is often divided, by means of conventional clock divider circuits, to produce several lower-frequency clock signals. In such crystal-controlled pacemakers, all time intervals are measured in units of clock cycles. For example, time intervals may be measured with a binary counter with the 32,768-Hz crystal oscillator signal applied to its clock input; a one-second interval, then, would be measured by causing the binary counter to count from 1 to 32,768.

Many of the time intervals which are relevant to a pacing algorithm (such as base pacing rate, A-V delay, refractory periods, blanking periods, and so on) have durations on the order of magnitude of tens or hundreds of milliseconds or so. For example, a cardiac cycle is typically on the order of one second (1000-mSec), a typical A-V delay value is 120 to 150-mSec, a typical refractory period may be 300-mSec, and a typical upper rate limit may be 400-mSec or so. If time intervals up to one second were to be measured in terms of numbers of cycles of a 32,768-Hz clock, a 15-bit binary counter would be required. On the other hand, if a slower clock were used, a counter with fewer bits would be required to measure such intervals. If a 32,768-Hz crystal oscillator is used, therefore, there will be a cost, in the form of additional circuitry required either to divide down the 32,768-Hz signal to slower frequencies, or to count 15-bit binary values. This additional circuitry could potentially increase the size, weight, and/or current consumption of the implanted device. In addition, the crystal itself is a relatively delicate component which requires care in handling and attachment in the manufacturing process. The implantable-grade crystal is an expensive component and adds "real estate" or size to the pacemaker hybrid circuit. In addition, the crystal oscillator and binary counter divide chain (15-bits) typically consumes several microamps of current from the pacemaker battery.

It is believed by the inventors, therefore, that elimination of the crystal oscillator in an implanted device would be advantageous in terms of the potential reduction of production costs, as well as potential size and weight reduction and increased battery longevity. In accordance with one aspect of the present invention, an ultra low-frequency (i.e., 10-Hz) oscillator circuit is utilized in place of the typically much higher-frequency crystal oscillators found in prior pacemakers. Circuit size is minimized since the number of clock cycles occurring during any relevant time interval will be smaller for a slower clock than for a much faster one. The need for clock dividing circuitry is also avoided.

Another aspect of implantable medical devices which is a subject of the present invention is the programming and telemetry system. In many prior implantable devices, programming is accomplished by communicating to the implanted device digital information identifying at least the parameter to be programmed and the desired parameter value to be programmed. This information is typically in the form of binary digital data which is radio-frequency modulated and transmitted to an antenna within the implanted device. In the implanted device, the modulated signal is demodulated, and the digital information is decoded. For example, the parameter to be programmed might be identified with an eight or sixteen bit binary word, and the desired parameter value may be represented with a second eight or sixteen bit binary word. Other information, such as an identification of the implanted device, verification codes, error correction codes, access verification codes, and so on, may also be communicated to the device during programming. In addition, the transmitted information may include initialization data to reduce the possibility of inadvertent programming of the device. One programming transaction, therefore, can involve the communication to the implanted device of tens or even hundreds of binary digital bits.

Typical telemetry systems require an antenna and a magnetic reed switch to allow communication with the external programmer. Both of these components are fragile and require special handling in the manufacturing process. Additionally, both components require hybrid "real estate" and thus increase the size and cost of the pacemaker.

A radio frequency telemetry system, while having the advantage of allowing large amounts of data to be communicated to the implanted device very quickly, can be costly not only in economic terms, but also in terms of the space it consumes in the implanted device, the power consumed in receiving and demodulating the radio frequency signals, and its weight. It is believed by the inventors, therefore, that it would be advantageous to provide a programming system which does not utilize radio frequency telemetry but still allows communication of the necessary information to the implanted device.

Yet another element of implantable medical devices to which the present invention relates is the memory subsystem for storing programmed parameter values. Many prior pacemakers are primarily digital rather than analog in their operation. Programmed parameter values are provided to such devices in digital binary format, as described above. The digital information may then be stored in random-access memory (RAM) or the like, and extracted therefrom when needed by the device's digital control circuitry. It is believed by the inventors, however, that recently developed analog storage devices may be advantageously applied in implantable medical devices in place of digital storage devices.

For example, in some prior art implantable devices, programmable parameter values are received by and stored in the pacemaker in digital form. In some cases, the stored parameter value may be used by the implanted device in digital form, such as to preset a binary counter or to compare with a counter values. In other cases, the digital parameter value is first applied to a digital-to-analog converter (DAC), and the analog output from the DAC used as a reference voltage for a voltage-controlled component of the device. If a parameter value must be in analog form to be used by the implanted device, the need for a DAC would be eliminated if the parameter value could be stored in analog, rather than digital form.

Additionally, digital data is typically stored in volatile memory (RAM) and may be lost or contaminated (flawed) during EMI, cautery, or defibrillation procedures. To prevent dangerous operation, typical prior art pacemakers have "power-on reset" (POR) circuitry to reset the device's parameters to a "typical" set of values. This circuitry adds complexity and cost to the implanted device and may cause non-optimal function if the RAM contents have been reset.

BRIEF DESCRIPTION OF THE DRAWINGS

The foregoing and other aspects of the present invention will be best appreciated with reference to the detailed description of a specific embodiment of the invention, which follows, when read in conjunction with accompanying drawings, wherein:

FIG. 11 is a schematic diagram illustrating a prior art bias current circuit for the pacemaker shown in FIG. 1 which requires a variable resistor connected to a bonding pad in parallel with a capacitor.

FIG. 12 is a schematic diagram illustrating the programmable bias current circuit which replaces the prior art bias current circuit shown in FIG. 11.

DETAILED DESCRIPTION OF A SPECIFIC EMBODIMENT OF THE INVENTION

Figure 1:
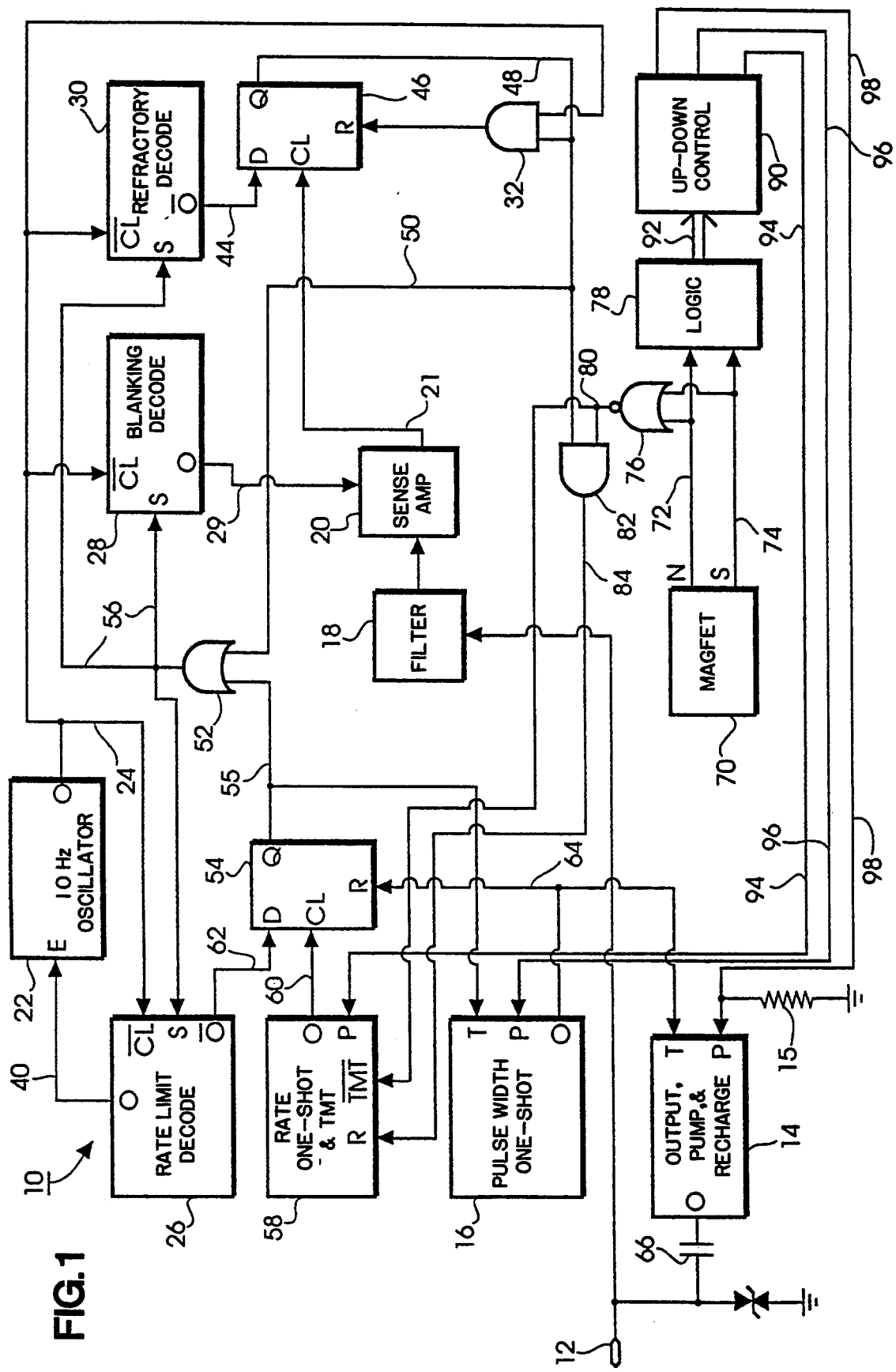
FIG. 1 is a diagram in block form of a pacemaker in accordance with one embodiment of the present invention.

FIG. 1 is a block diagram depicting the major components of a small, lightweight, limited-function pacemaker 10 in accordance with one embodiment of the present invention. Pacemaker 10 is preferably of the implantable type, being encased within a hermetically sealed housing (not shown in the Figures) and coupled to a patient by means of a cardiac lead (also not shown in the Figures). The cardiac lead is coupled via a conventional feedthrough arrangement to the hermetically sealed circuitry of pacemaker 10, in keeping with common practice in the art. The point of connection between a pacemaker lead and the circuitry of pacemaker 10 is designated with reference numeral 12 in FIG. 1.

It is to be understood throughout the present disclosure that various internal electronic components comprising pacemaker 10 are coupled to a power source, such as a battery, not shown in the Figures. For the sake of clarity, the connection of each of the components with a power source is not shown. It is believed that a commercially available magnesium oxide ($MnO_2$) camera battery or the like is a suitable power supply for the purposes of the present invention, having acceptable output voltage and current levels, useful longevity, size, and weight.

Pacemaker 10 includes an output and pump circuit 14 which delivers electrical stimulating pulses to the pacemaker lead at point 12 under control of a pacing trigger signal issued by a pulse width one-shot 16, as shall be hereinafter described in greater detail. Output and pump circuit 14 may correspond generally to the output amplifier disclosed in U.S. Pat. No. 4,476,868 issued to Thompson et al. on Oct. 16, 1984, which patent is hereby incorporated by reference into the present disclosure. However, modern output circuits are implemented in CMOS, and the inventors believe that the output circuit is not critical to the invention. Thus, any output circuit may be substituted for output and pump circuit 14. Particularly, the output and pump circuit from the Mealtronic Bravo ™ pacemaker, presently commercially available in Europe, may be used. Additionally, output and pump circuit 14 further includes a programmable amplitude control circuit to be hereinafter described which allows for programming of the amplitude of output pulses from output and pump circuit 14.

The patient's intrinsic electrical cardiac activity is monitored by means of a filter circuit 18 and a sense amplifier 20. Raw intrinsic electrical cardiac signals from the patient's heart are conducted on the pacemaker lead to point 12, and further conducted to the input of filter circuit 18. Filter circuit 18 performs basic band-pass filtering operations on the raw electrical cardiac signal, and provides the conditioned signal to sense amplifier 20. Sense amplifier 20 may be one of the various types of sense amplifiers known in the prior art. Particularly, the sense amplifier circuit from the Mealtronic Bravo ™ pacemaker may be used. The output of sense amplifier 20 is conducted on line 21 to the clock input of flip-flop 46. As with conventional sense amplifiers, sense amplifier 20 produces positive-going pulse on line 21 when a cardiac event (atrial or ventricular, depending upon lead placement) is sensed. Sense amplifier 20 is prevented from receiving pacing artifacts through operation of a blanking circuit 28, to be hereinafter described.

While specific embodiments of sense amplifier 20 and output/pump circuit 14 have been identified herein with reference to prior patents, this is done for the purposes of illustration only, and is not intended to limit the scope of the present invention to particular implementations of these circuits. It is believed by the inventors that the selection of a particular type of sense amplifier and output circuit is not critical to the present invention so long as sense amplifier 20 and output circuit 14 provide the necessary means for detecting intrinsic electrical cardiac activity, and generating suitable cardiac stimulating output pulses, respectively, in conformance with the remainder of the present disclosure.

In accordance with one aspect of the present invention, operation of pacemaker 10 occurs in synchronization with a slow, e.g., 10-Hz, master timing clock signal generated by 10-Hz oscillator circuit 22 in FIG. 1. 10-Hz oscillator 22 is enabled via line 40 from the output of rate limit decode circuit 26. As shown in FIG. 1, the timing clock signal generated by circuit 22 is applied via line 24 to a rate limit decode circuit 26, blanking decode circuit 28, and a refractory decode circuit 30. Also, the 10-Hz timing clock signal is applied to one input of an AND gate 32, as shall be hereinafter described in more detail.

Rate limit decode circuit 26, blanking decode circuit 28, and refractory decode circuit 30 define an upper rate limit period, a blanking period, and a refractory period, respectively, by counting 10-Hz clock cycles provided on line 24. The blanking decode circuit defines a 'blanking interval' which follows every sensed or paced cardiac event. During the blanking interval, the output signal O from blanking circuit 28 goes high; this signal is conducted on line 29 to a DISABLE input of sense amplifier 20. The blanking interval is indicated by a logical high level pulse of the signal on line 29. In this way output signals from sense amplifier 20 are prevented from affecting operation of pacemaker 10.

In the presently preferred embodiment of the invention, it is believed that a blanking interval on the order of 100-mSec or so is appropriate. In that case, blanking decode circuit 28 would define the blanking interval as lasting for one 10-Hz clock cycle. It is to be understood that a blanking period comprising a greater number of clock cycle counts may be defined, depending upon the desired length of the blanking interval and the actual oscillation rate of circuit 22.

Refractory decode circuit 30 defines a refractory period which follows every sensed or paced cardiac event. The refractory period is indicated by a logical low level refractory output signal $\overline{O}$ on line 44, which signal is applied to the D input of a D flip-flop 46. The output on line 21 from sense amplifier 20 is applied to the clock (CL) input of flip-flop 46.

Refractory decode circuit 30 measures the refractory period by counting 10-Hz clock cycles from line 24, just as blanking decode circuit measures the blanking interval. In the presently preferred embodiment of the invention, it is believed that a refractory period on the order of 300-mSec or so is appropriate; thus, refractory decode circuit can define the refractory period as lasting for three 10-Hz clock cycles. After the refractory period has expired, the signal O— on line 44 returns to a logical high level; at this point, the assertion of the signal on line 21, caused by a sensed or paced event, clocks the output of D flip-flop 46 on line 48 to a logical high level.

The signal on line 48 is applied to one input of AND gate 32; the other input of AND gate 32 receives the 10-Hz clock signal, as previously noted. After expiration of the refractory period, the line on line 48 will go to a logical high level upon detection of a sensed event or upon generation of an output pulse. Then, the next positive excursion of the 10-Hz clock signal will bring the output of AND gate 32 to a logical high level. The output of AND gate 32 is conducted on line 50 to the reset (R) input of flip-flop 46; thus, when the signal on line 50 goes high following expiration of the refractory period, the output of flip-flop 46 is brought to a logical low level.

The output signal from flip-flop 46 on line 48 is also applied to one input of an OR gate 52, which other input receives the output of a D flip-flop 54. The output of OR gate 52 is conducted on line 56 to the set (S) inputs of decode circuits 26, 28, and 30. A positive pulse on line 56 thus sets and restarts the upper rate limit interval, blanking interval, and refractory interval.

Rate limit decode circuit 26 defines an upper rate limit for delivery of stimulating pulses by pacemaker 10. In the presently disclosed embodiment of the invention, it is believed that an upper rate limit of one pacing pulse every 400-mSec, or a maximum pacing rate of 150-PPM, is appropriate. In this case, rate limit decode circuit 26 defines an upper rate limit interval which lasts for four 10-Hz clock cycles. The output $\overline{O}$ from rate limit circuit 26 goes low for 400-mSec following each sensed or paced cardiac event. This signal is applied on line 62 to the data (D) input of D flip-flop 54. During the 400-mSec interval, rate one-shot 58 is prevented from causing the assertion of the Q output from D flip-flop 54 as shall hereinafter be described. After the 400-mSec upper rate limit interval has elapsed following a paced or sensed cardiac event, the $\overline{O}$ output signal from rate limit circuit 26 returns to a logical high level.

As previously noted, the sense amplifier output signal is applied via line 21 to the clock input of flip-flop 46. With this arrangement, a sensed electrical cardiac event will result in a positive pulse being applied on line 21 to the clock input of flip-flop 46, as previously described. In view of the foregoing description of flip-flop 46, decoders 28 and 30, AND gate 32, and OR gate 52, it will be apparent to one of ordinary skill in the pacemaker art that a sensed electrical cardiac event will lead to the restarting of the blanking and refractory periods.

With continued reference to FIG. 1, a rate one-shot and threshold margin test circuit 58 (hereinafter referred to simply as rate/TMT circuit 58) determines the base pacing rate, which is the rate at which pacing pulses will be delivered by pacemaker 10 in the absence of sensed intrinsic cardiac activity. Rate/TMT one-shot 58 includes a retriggerable monostable multivibrator which produces an output signal O on line 60. A rising-edge transition of the signal on line 84 that is applied to the reset (R) input of rate/TMT circuit 58 resets and restarts the timing of rate/TMT circuit 58. The timing and/or interval between pulses produced by rate/TMT circuit 58 is programmable, as shall be hereinafter described, within a range from 460- to 1200-mSec (i.e., 50-PPM to 130-PPM). So long as a rising-edge transition appears at the R input of rate/TMT circuit 58 more frequently than the programmed output pulse interval, the output signal on line 60 will stay at a logical low level. Only when no rising edge appears at the R input to circuit 58 for a period longer than the programmed rate interval will the output on line 60 go to a logical high level.

Rate limit decode circuit 26 prevents pacing pulses from being delivered above a predetermined upper rate limit. This is because a rising edge in the output signal on line 60 will cause the output of flip-flop 54 to go to a logical high level only when the output from rate limit decode circuit 26 is at a logical high level, indicating that the upper rate limit interval has expired. Rate limit decode circuit 26 is set by the output of OR gate 52, each time a sensed or paced cardiac event occurs. When decode circuit 26 is set, its output signal on line 62 goes to a logical low level, where it remains until decode circuit 26 counts the number of 10-Hz clock cycles in the predetermined upper rate limit interval. When this count is reached, indicating that the upper rate limit interval has expired, the signal on line 62 goes high. Thereafter, the next rising edge of the rate one-shot signal on line 60 will bring the output of flip-flop 54 to a logical high level.

The output of flip-flop 54 is conducted on line 55 to a second input of OR gate 52. The output of flip-flop 54 is also conducted to the trigger (T) input of pulse width one-shot 16. A rising-edge transition of the rate one-shot signal on line 60 will trigger delivery of a pacing pulse if rate limit decode circuit 26 indicates that the upper rate limit interval has expired. If the upper rate limit interval has expired when a rising edge of the signal on line 60 occurs, the output of flip-flop 54 goes high; this triggers pulse width one-shot 16, producing a pulse on line 64 whose duration defines the pulse width of a pacing pulse to be produced by output and pump circuit 14. The duration of pulses produced by pulse width one-shot 16 on line 64 is programmable within a range from 0.1- to 1.0-mSec, in a manner to be hereinafter described in greater detail with reference to FIGS. 6–8.

Output pulses from pulse width one-shot 16 are conducted on line 64 to the trigger input of output and pump circuit 14. For the duration of the pulse on line 64, output and pump circuit 14 applies a cardiac stimulating voltage to the patient's heart via coupling capacitor 66. The amplitude of this pacing pulse is programmable, as will be hereinafter described.

Output pulses from pulse width one-shot 16 are also applied on line 64 to the reset (R) input of flip-flop 54. Thus, when a pacing pulse is delivered, the signal on line 55 goes from a logical high to a logical low level. In this way, the transition on line 55 causes the blanking and refractory intervals to be restarted, in the manner previously described with reference to flip-flop 46, AND gate 32, OR gate 52, and decode circuits 28 and 30.

In accordance with another aspect of the present invention, selected operational parameters of pacemaker 10 of the presently disclosed embodiment are non-invasively programmable by means of a novel programming arrangement. In order to eliminate the need for space and energy consuming radio-frequency telemetry circuitry and components, the programming scheme in the presently disclosed embodiment of the invention utilizes a solid state semiconductor device which is sensitive to application of an external magnetic field. If a split-drain field effect transistor, also called a 'MAGFET', is included in the circuitry of pacemaker 10, the MAGFET can be used to detect the presence of an externally positioned magnet, in much the same way as a magnetically-actuated reed switch has been used for pacemakers in the prior art.

A solid-state magnetic field sensor (MAGFET) suitable for use in an implantable medical device telemetry system is disclosed in a co-pending U.S. patent application Ser. No. 07/982,132 to Wahlstrand et al. and assigned to the assignee of the present invention. The Wahlstrand et al. application is hereby incorporated herein by reference in its entirety. The use of a MAGFET-based magnetic sensor is believed to have advantages over a conventional magnetic reed-switch, which is a delicate mechanical component with a relatively high production cost and low production yield.

Referring again to FIG. 1, pacemaker 10 includes a MAGFET circuit 70 such as is disclosed in the above-referenced Wahlstrand et al. application. As noted in the Wahlstrand et al. application, MAGFET circuit 70 is capable of discerning between external magnetic fields of two different polarity orientations (e.g., between a field oriented north-south and a field oriented south-north). Accordingly, MAGFET circuit 70 produces two output signals, N (north) on line 72, and S (south) on line 74. The N signal is asserted, for example, upon detection by MAGFET circuit 70 of an applied magnetic field of N-S orientation. Likewise, the S signal is asserted upon detection of an applied magnetic field of S-N orientation. The N and S signals are applied to the inputs of a NOR gate 76, and are also applied as inputs to a logic circuit 78, the function of which will be hereinafter described in greater detail. In the absence of an applied magnetic field, both output signals N (line 72) and S (line 74) are at a logic zero level.

The programming scheme of the presently disclosed embodiment of the invention is based upon detection of application of an external magnetic field, such as by positioning a magnet on the patient's skin in close proximity to the implanted device. As in the case with many prior art pacemakers, detection of an external magnetic field results in pacemaker 10 entering an asynchronous pacing mode, with electrical cardiac sensing being temporarily disabled. To this end, the output on line 80 from NOR gate 76 is a signal which is normally at a logical high level, but which falls to a logical low level in response to detection of a magnetic field of either N-S or S-N orientation. Thus the signal on line 80 effectively constitutes a 'magnet not present' signal; this signal is applied to one input of an AND gate 82, the other input of which receives the output from refractory flip-flop 46. The output from AND gate 82 is conducted on line 84 to the reset (R) input of rate/TMT one-shot 58. The 'magnet not present' signal on line 80 is also conducted to the $\overline{\text{TMT}}$ input of rate/TMT one-shot 58.

One feature of the presently disclosed embodiment of the invention is that the number of programmable functions of pacemaker 10 is limited, in order to minimize the amount of programming and telemetry circuitry required. In particular, it is believed that three programmable values is sufficient. For example, in the presently disclosed embodiment the base pacing rate, pacing pulse width, and pacing pulse amplitude parameters are programmable within selected ranges. In this case, other parameters which might be programmable in other pacemakers, such as sense amplifier sensitivity, refractory periods, and so on, are preset to fixed nominal values that are likely to be suitable for most patients. It is contemplated by the inventors, however, that a different set of three programmable values, such as base pacing rate, pacing pulse amplitude, and sense amplifier sensitivity, may be chosen as the programmable parameters, with remaining parameter values such as pacing pulse width preset to fixed nominal values. While a particular set of three programmable parameters is defined herein, it is believed by the inventors that other combinations of programmable parameters may be defined in practicing the present invention.

In order to separately program three different parameter values, there must be some arrangement for selecting one of these values to be programmed. In some prior pacemakers using radio-frequency telemetry for programming, identification of the parameter to be programmed has been accomplished by simply transmitting a code to the pacemaker identifying the programmed parameter to be changed. In the presently disclosed embodiment of the invention, however, all communication with pacemaker 10 must be accomplished by placement of a magnet within sensor range of MAGFET 70. For pacemaker 10, identifying a parameter to be programmed involves initially placing a programming magnet within sensor range of MAGFET 70, and then removing and replacing the magnet one or more times, with different numbers of removal/replacement cycles identifying different parameters.

Logic 78 receives both the N and S signals from MAGFET circuit 70, and can therefore respond to any detection by MAGFET 70 of an external magnet. Upon assertion of the signal at its TMT input, rate/TMT one-shot 58 performs a so-called threshold margin test (TMT), which assists the physician in determining whether the currently programmed pulse width and pulse amplitude settings are sufficient to achieve 'capture' of the patient's heart. The TMT in the presently disclosed embodiment of the invention may be one such as is disclosed in U.S. Pat. No. 4,273,132 issued to Hartlaub on Jun. 16, 1981, incorporated herein by reference in its entirety. 'Capture' refers to the effect that a pacing pulse has on the patient's heart. If a pacing pulse has sufficient amplitude and duration to overcome the patient's stimulating threshold and cause a cardiac contraction, this is referred to as 'capture'. If a pacing pulse has insufficient amplitude or pulse width to overcome the patient's stimulation threshold and does not cause a cardiac contraction, this is referred to as a lack of capture.

The threshold margin test performed by rate/TMT one-shot 58 involves delivering several (e.g., three) asynchronous pacing pulses in a row at a higher than normal rate. A physician observes the patient's cardiac activity on an EKG monitor during a threshold margin test, and can thereby observe whether or not the three pacing pulses each resulted in a cardiac contraction. If not, the physician can increase either the programmed pulse width or pulse amplitude, so that the pacing pulses have enough energy to overcome the patient's stimulation threshold.

After rate/TMT one-shot 58 performs the threshold margin test, pacemaker 10 will begin asynchronous pacing at a nominal rate, e.g., seventy PPM, for as long as a magnet continues to be detected by MAGFET circuit 70. According to the presently disclosed embodiment of the invention, the first removal and replacement of the magnet after the threshold margin test puts pacemaker 10 (specifically, logic circuit 78) into a rate programming mode in which base pacing rate is programmed. The second magnet removal/replacement cycle puts pacemaker 10 in an amplitude programming mode in which the pacing pulse amplitude is programmed, while a third magnet removal/replacement cycle following the TMT puts pacemaker 10 in a pulse width programming mode in which pacing pulse width is programmed.

Programming any of the three programmable parameters is accomplished by first causing the pacemaker to perform the TMT and enter the asynchronous (magnet) mode, and then performing the appropriate number (one, two, or three) of magnet removal/replacement cycles to bring pacemaker 10 into the desired programming mode. Once in the desired programming mode, pacemaker 10 will adjust the selected parameter up or down, by an incremental amount each pacing cycle, depending upon the polarity of the detected magnetic field. For example, in rate programming mode (initiated by entering magnet mode and then removing and replacing the magnet once), pacemaker 10 will increase the pacing rate by an incremental amount each pacing cycle so long as a N-S oriented magnetic field is detected. Conversely, pacemaker 10 will decrease the pacing rate by an incremental amount each pacing cycle so long as a S-N oriented magnetic field is detected while in rate programming mode. Programming the pacing rate to a desired level is thus accomplished by maintaining a S-N or N-S oriented magnetic field over MAGFET circuit 70 for enough pacing cycles to reach the desired level. When the desired rate is reached, rate programming is terminated by merely removing the magnet.

So that the physician can verify that programming of the desired parameter occurs successfully, pacemaker 10 in accordance with the presently disclosed embodiment of the invention delivers an additional one or more pacing pulses in rapid succession during each pacing cycle during programming. During normal (i.e., non-programming) operation, each pacing stimulus delivered to the patient's heart comprises a single pulse having the programmed width and amplitude. When pacemaker 10 is put into one of the programming modes, however, each pacing stimulus delivered to the patient's heart comprises two or more pulses in rapid succession, for example, 5-mSec apart.

Consider, for example, programming of the pacing rate in pacemaker 10. Pacemaker 10 is put into rate programming mode as described above, by placing a programming magnet over pacemaker 10, then removing and replacing the magnet once after the TMT is performed. Then, depending upon the polarity of the applied magnetic field, the pacing rate is adjusted up or down by an incremental amount during each subsequent pacing cycle. While this occurs, each pacing stimulus delivered to the patient's heart will comprise two electrical pulses, 5-mSec apart, having the currently programmed pulse width and pulse amplitude. The patient is preferably connected to an EKG monitor during pacemaker programming. In this way, the physician can verify that rate programming is occurring by noting artifacts of the double-pulse pacing stimulus delivered each cardiac cycle. It has been shown that delivering multiple pacing pulses in rapid succession has little or no physiological impact on the patient, and pacing stimuli return to single pulses when the magnet is removed from the patient and programming is terminated.

When pacemaker 10 is put into pulse amplitude programming mode, each pacing stimulus comprises three electrical pulses, 5-mSec apart, at the programmed width and amplitude. Similarly, when pacemaker 10 enters pulse width programming mode, each pacing stimulus comprises four electrical pulses delivered 5-mSec apart. Thus, during programming, the physician can identify the parameter being adjusted by counting the number of pulses delivered each cardiac cycle.

Figure 2A:
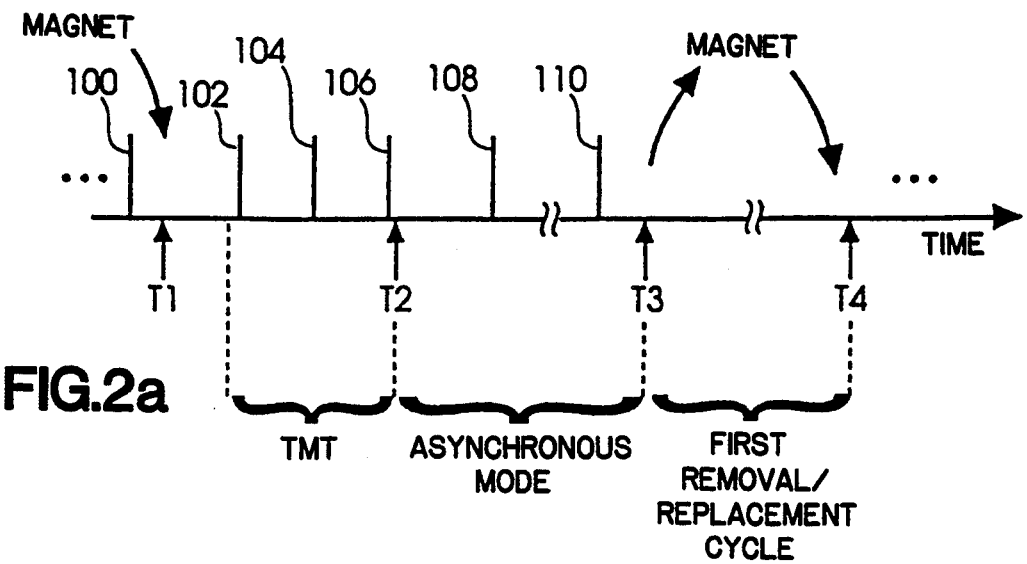
FIGS. 2a, 2b, and 2c are time lines showing the timing of pacing pulses during programming of the pacemaker of FIG. 1.
Figure 2B:
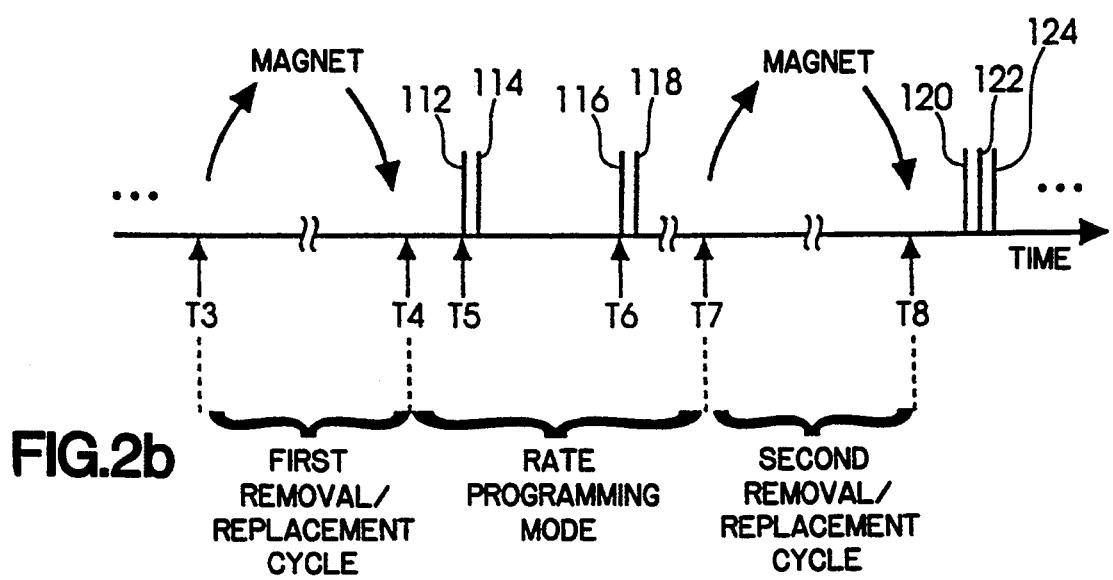
Figure 2C:
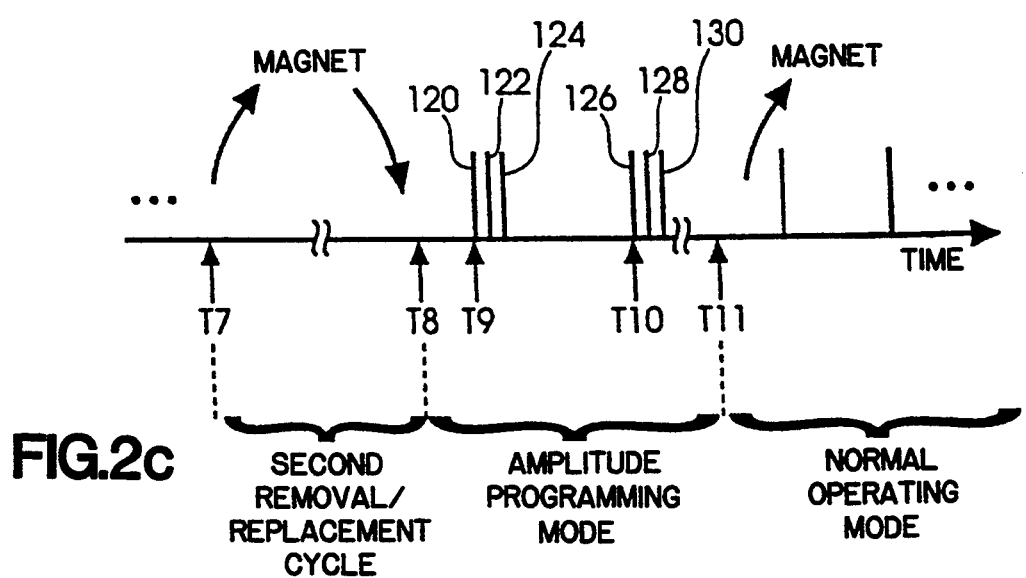

The sequence of events involved in programming pacemaker 10 may be better understood with reference to the time lines of FIGS. 2a, 2b and 2c. In FIGS. 2a, 2b, and 2c, pacing pulses are represented by vertical lines such as those designated 100 and 102; this corresponds roughly with the appearance of pacing artifacts viewed on an EKG monitor. In FIG. 2a, it is assumed that pacemaker 10 is operating normally up to time T1, at which time a programming magnet is applied. In response to detection of the programming magnet, pacemaker 10 will perform the TMT. The TMT involves the delivery of three pacing pulses 102, 104, and 106 at an asynchronous rate of, for example, 70-PPM. Artifacts of these three pacing pulses may be observed by a physician on an EKG monitor, so that the physician may determine whether the pacing pulses exceed the patient's pacing threshold.

After the TMT, beginning at time T2, pacemaker 10 enters the asynchronous mode, in which pacing pulses such as 108 and 110 are delivered at a nominal asynchronous rate, for example 70-PPM. It is to be understood that the interval of asynchronous pacing between time T2 and time T3 in FIG. 2a may last an indefinite period of time, so long as the programming magnet remains in place.

At time T3, the magnet is removed, and at time T4 the magnet is replaced. This constitutes one magnet removal/replacement cycle. During the time interval T3 to T4, one or more pacing pulses may or may not be delivered. It is not necessary for the removal/replacement cycle to occur within a single cardiac cycle, so long as replacement follows within a reasonable amount of time (e.g., 2.0-sec or so) after removal.

When the first removal replacement cycle has been detected following time T4, pacemaker 10 will enter the rate programming mode. The removal/replacement cycle beginning at time T3 and ending at time T4 is shown again in FIG. 2b. As shown in FIG. 2b, during rate programming mode, each pacing stimulus comprises two pulses, such as pulses 112 and 114, or pulses 116 and 118, separated by 5-mSec. Thus, if pacing pulse 112 is delivered at time T5, pacing pulse 114 is delivered at time (T5+5-mSec). (It is to be noted, of course, that FIGS. 2a, 2b, and 2c are not drawn to scale.)

As previously described, while pacemaker 10 is in rate programming mode, the programmed pacing rate is adjusted up or down by an incremental amount $\Delta_R$ each cardiac cycle. In FIG. 2b, it will be assumed that the magnet is placed in a N-S orientation, corresponding to increasing the pacing interval. Thus, if the initial programmed pacing interval prior to time T1 was 1000-mSec (corresponding to a pacing rate of 60-PPM), at time T5 the pacing interval is increased to $(1000+\Delta_R)$-mSec and at time T6 the pacing interval is increased to $(1000+2\Delta_R n)$-mSec. If, on the other hand, the programming magnet at time T4 has a S-N orientation, at time T5 the pacing interval would be decreased to $(1000-\Delta_R)$-mSec and at time T6 decreased to $(1000-2\Delta_R)$-mSec.

During the time interval from T7 to T8 in FIG. 2b, a second magnet removal/replacement cycle is performed. As before, one or more pacing pulses may be delivered during the interval from T7 to T8. This second removal/replacement cycle puts pacemaker 10 in amplitude programming mode, beginning at time T8. The removal/replacement cycle occurring between T7 and T8 from FIG. 2b is shown again in FIG. 2c. Pacing stimuli delivered during amplitude programming mode comprise three pulses, such as the three pulses 120, 122, and 124, delivered 5-mSec apart beginning at time T9. While pacemaker 10 is in amplitude programming mode, the programmed pacing pulse amplitude is adjusted up or down (depending upon the orientation of the programming magnet) by an incremental amount $\Delta_A$ each cardiac cycle. Assuming a N-S orientation of the magnet (corresponding to increasing the amplitude), if the initial programmed pulse amplitude at time T1 was 3.0-volts then at time T9 the programmed amplitude is increased to $(3+\Delta_A)$-volts, and at time T10 the programmed amplitude is increased to $(3+2\Delta_A)$-volts.

At time T11 in FIG. 2c, the programming magnet is removed. If no magnet replacement is detected within 2.0-sec thereafter, the programming session is ended and pacemaker 10 resumes operation at the newly programmed parameters. Of course, it is to be understood that if another removal/replacement cycle occurred beginning at time T11 in FIG. 2c, this would cause pacemaker 10 to enter the pulse width programming mode. Each pacing stimulus delivered during pulse width programming mode would comprise a sequence of four pacing pulses, 0.5-mSec apart, and the pulse width would be adjusted up or down by an incremental amount $\Delta_P$ during each cardiac cycle.

One advantage of the programming technique of the presently disclosed embodiment of the invention is that all changes in programmed parameters are accomplished in a series of small, incremental or decremental steps. It is generally believed that sudden and drastic changes in programmed parameters can be detrimental to the patient and should be avoided. For example, it would be undesirable for pacing rate for a pacemaker to be suddenly reduced from a high rate, say 120 pulses per minute (PPM), to a much lower rate, say 60 PPM, since the patient's intrinsic heart rate would probably never undergo such an extreme unphysiologic change. Abrupt parameter changes can therefore have deleterious effects on the patient. By increasing or decreasing programmed parameters by only an incremental amount during each pacing cycle, such sudden parameter changes are prevented.

Logic circuit 78, as previously noted with reference to FIG. 1, is responsive to the N and S signals from MAGFET circuit 78 to detect magnet placements and removals, and to initiate the desired parameter changes. Logic circuit 78 issues control signals to an up/down control circuit 90 via a plurality of control lines designated collectively as 92 in FIG. 1. Logic circuit 78 includes digital logic circuitry for detecting magnet removal and replacement cycles; this circuitry will not be described herein in detail, since it is believed by the inventors that implementation of such circuitry would be a matter of routine to a person of ordinary skill in the art of logic design. For the purposes of the present disclosure it will be assumed that circuitry 78 detects magnet removal and replacement cycles, and asserts various control signals in response thereto. For example, in response to detection of one magnet removal/replacement cycle, logic circuit 78 would assert a control signal to up/down control 90 indicating that the pacing rate should be incrementally adjusted. Another control signal, derived from the N and S magnet polarity signals on lines 72 and 74 would be asserted to indicate whether the pacing rate is to be adjusted up or down.

In accordance with one feature of the present invention, up/down control circuit 90 produces a plurality of output signals which are conducted on lines 94, 96, and 98 to rate/TMT circuit 58, pulse width one-shot 16, and output/pump circuit 14, respectively. The signals on lines 94, 96, and 98 are analog reference currents which will be described in more detail subsequently with reference to FIG. 6. Lines 94, 96, and 98 are applied to the program (P) inputs of rate/TMT circuit 58, pulse width one-shot 16, and output/pump circuit 14, respectively, as shown in FIG. 1. The reference currents on lines 94 and 96 determine the duration of output pulses from the respective one-shots 58 and 16, and hence determine the pacemaker's pacing rate and pulse width. The reference current on line 98 determines the output pulse amplitude from the output/pump circuit 14 by generating a reference voltage on resistor 15. This reference voltage is used in conjunction with a comparator and a charging circuit in output/pump circuit 14 to charge an output capacitor to a programmed amplitude as is well known in the art.

For example, in the case of the pacing rate parameter, up/down control circuit 90 provides a reference current on line 94 to the P input of rate/TMT circuit 58. An incremental decrease in the reference current level on line 94 results in an increase in the pacing interval established by rate/TMT circuit 58; likewise, an incremental increase in the reference current level on line 94 results in an incremental decrease in pacing interval established by rate one-shot 58. Pulse width one-shot 16 and output/pump circuit 14 are controlled in a similar fashion with the reference current provided on lines 96 and 98, respectively.

Figure 3:
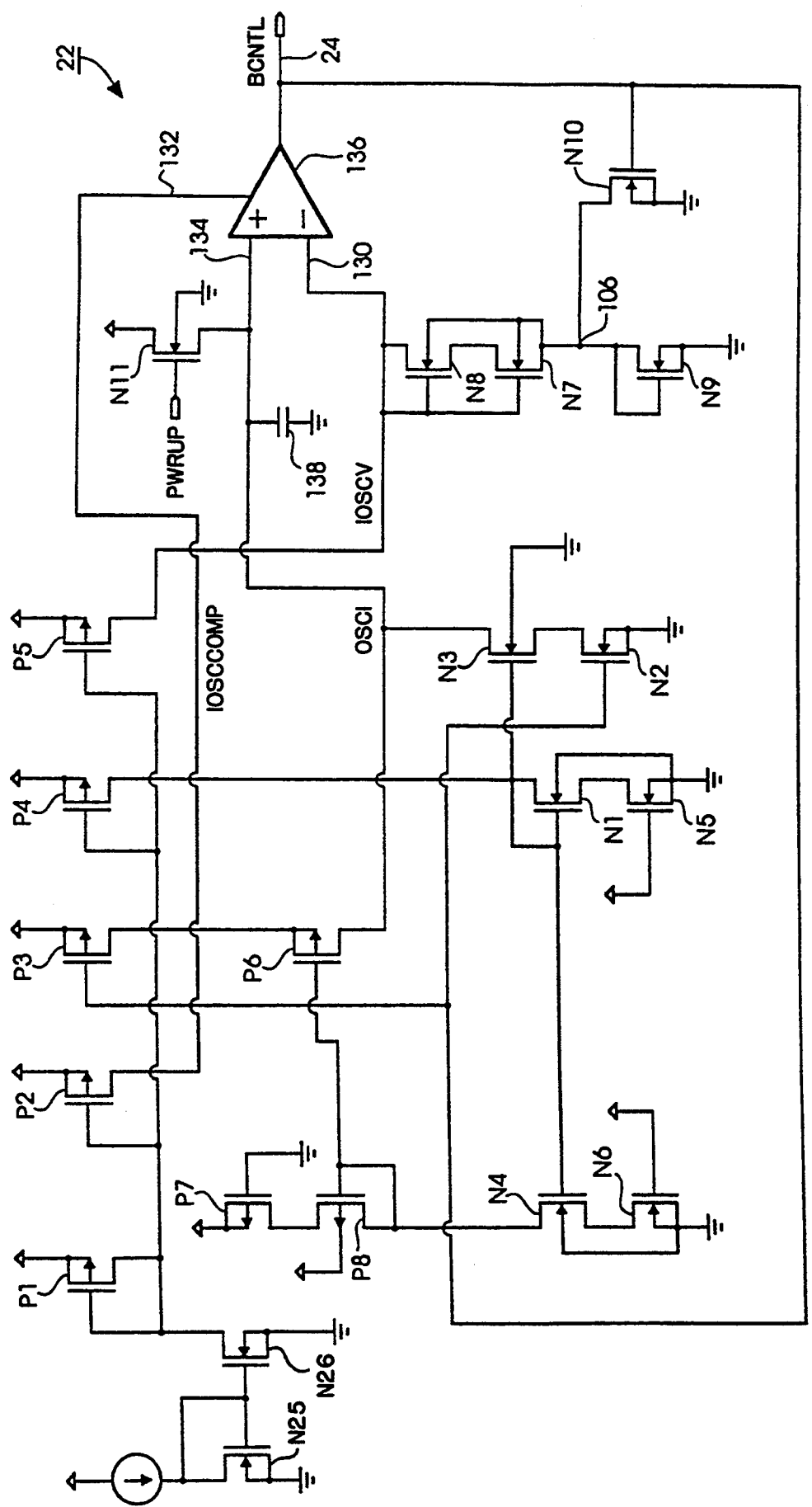
FIG. 3 is a schematic diagram of the oscillator circuit in the pacemaker of FIG. 1.

FIG. 3 is a schematic diagram of a 10-Hz oscillator circuit 22. In the presently disclosed embodiment of the invention, the circuitry of pacemaker 10 is preferably implemented in the form of one or more integrated circuits fabricated using conventional CMOS processes, although other implementations may also be suitable. In the Figures, transistors are identified with reference designators beginning with either a "P" or an "N", corresponding to P-type and N-type field-effect transistors (FETs), respectively. The channel sizes of each of the transistor devices shown in the Figures are set forth in the following Table 1:

TABLE 1

| DEVICE | CHANNEL SIZE (length/width, in microns) |
| --- | --- |
| P1 | 7/16 |
| P2 | 5 × 7/16 |
| P3 | 4/3 |
| P4 | 7/16 |
| P5 | 7/16 |
| P6 | 4/12 |
| P7 | 4/3 |
| P8 | 4/12 |
| P9 | 4/7 |
| P10 | 4/7 |
| P11 | 4/7 |
| P12 | 4/7 |
| P13 | 4/7 |
| P14 | 4/7 |
| P15 = P16 | 4/4 |
| P18 | 10 × 15/20 |
| P19 | 15/20 |
| P20 | 15/20 |
| P21 | 15/20 |
| P22 | 4/3 |
| P23 | 4/3 |
| P24 | 9/3 |
| P25 | 4/3 |
| P26 | 2 × 15/10 |
| P28 | 9/10 |
| N1 | 4 × 7/7 |
| N2 | 7/3 |
| N3 | 7/7 |
| N4 | 7/7 |
| N5 | 4 × 7/3 |
| N6 | 7/3 |
| N7 | 4/60 |
| N8 | 5 × 4/3 |
| N9 | 4/60 |
| N10 | 7/3 |
| N11 | 7/3 |
| N12 | 7/4 |
| N13 | 7/4 |
| N14 | 7/4 |
| N15 | 7/20 |
| N16 | 4 × 7/20 |
| N17 | 2 × 7/20 |
| N18 | 4/7 |
| N19 | 4/7 |
| N20 | 4/7 |
| N21 | 4/7 |

TABLE 1-continued

| DEVICE | CHANNEL SIZE (length/width, in microns) |
| --- | --- |
| N22 | 4/4 |
| N23 = N24 | 4/3 |
| N25 = N26 | 4/3 |
| N27 | 25/8 |
| N28 | 25/8 |
| N29 | 10 × 15/20 |
| N30 | 15/20 |
| N31 | 5/10 |
| N32 | 4/3 |
| N33 | 5/3 |
| N34 | 4/10 |
| N35 | 4/10 |

The oscillator circuitry of FIG. 3 produces three output bias signals, designated IOSCV (on line 130), IOSCCOMP (on line 132), and OSCI (on line 134). The OSCI signal on line 134 is applied to the non-inverting (+) input of a comparitor 136. OSCI line 134 is also tied to ground via a capacitor 138, which in the preferred embodiment has a capacitance value of 16.67-picofarads (pF). In FIG. 3 and the Figures which follow, a positive voltage $V_{DD}$ is applied to various points in the circuit. It is to be understood in the Figures that the designation '$V_{DD}$' corresponds to a connection to the positive voltage supply. The current source and transistors N25 and N26 form a current bias source of 1 nA for the oscillator circuit of FIG. 3.

The IOSCV signal on line 130 is applied to the inverting (−) input of comparitor 136. The IOSCV signal is also applied to the gates of transistors N7 and N8, and to the source of transistor N8. The IOSCCOMP signal on line 132 is applied to the input bias current terminal of amplifier 136. A PWRUP signal, which is asserted for a brief period of time when power is first applied to the circuitry of pacemaker 10, is applied to the gate of a transistor N11 in FIG. 3. It is common practice in the art to provide such a signal as PWRUP which is tied to various components of the implantable device for the purpose of preventing aberrant operation of the device when power is first applied to the circuitry, or when power is for some reason momentarily disrupted. The PWRUP initialization signal briefly holds certain signal lines in pacemaker 10 at desired levels while the pacemaker's circuitry settles in to a normal operational state. It is believed by the inventors that providing the PWRUP signal would be a matter of routine implementation to a person of ordinary skill in the field of implantable medical devices. Accordingly, the description of the PWRUP signal's function herein will be limited to its effect on components of pacemaker 10 relevant to the present invention, and it is to be understood that the PWRUP signal would probably be applied to other components of pacemaker 10 not described in detail herein, in accordance with common practice in the art.

Operation of oscillator circuit 22 is based upon the repeated charging and discharging of capacitor 138. When power is first applied to pacemaker 10, the initialization signal PWRUP is briefly asserted. As can be seen from FIG. 3, the assertion of PWRUP turns on transistor N11, holding the OSCI line at a positive voltage greater than that applied to input 130 of amplifier 136. As a result, the BCNTL output of amplifier 136 (which corresponds to an amplification of the voltage difference between the voltages at the (+) and (−) inputs to amplifier 136) also goes to a positive voltage. The BCNTL output signal is applied to the gate of transistor N10, and also feeds back to be applied to the gates of transistors N2 and P3 in FIG. 3. Transistor N10 turns on as a result of the positive BCNTL voltage, thereby effectively grounding the node designated as 106. This action causes the node designated as 130 (i.e., IOSCV) to be at a voltage equal to the sum of one N-channel threshold plus approximately 100-mV (i.e., the $V_{DS}$ of transistor N7); this voltage is established in this way to assure that the differential pair of comparator 136 remains in saturation.

As can be seen from FIG. 3, when BCNTL is high, transistor P3 is turned off—which disables the current source formed by transistor P6—and transistor N2 is turned on—which enables the current source formed by transistor N3. Thus, capacitor 138 is pulled down by current source N3 (this action is portrayed in FIG. 5a, which shows OSCI at $V_{DD}-0.5V$ (approximately 1 N-channel threshold below $V_{DD}$). When the voltage at OSCI falls below the voltage on the node designated as 130 (approximately one N-channel threshold plus 100-mV), BCNTL goes low, which causes transistors N10 and N2 to turn off and transistor P3 to turn on.

Figure 5A:
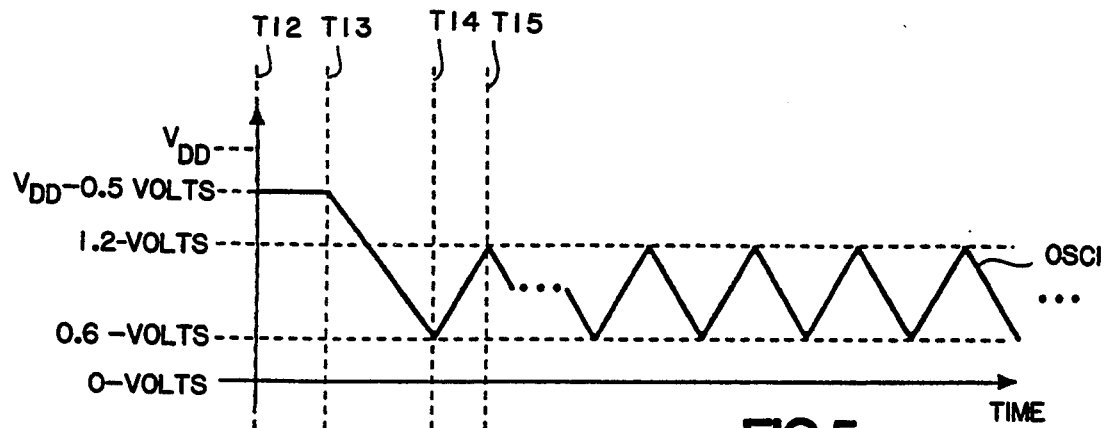
FIGS. 5a, 5b, and 5c are timing diagrams showing signal levels for selected signals present in the clock circuit of FIGS. 3 and 4.

Thus, the voltage on the node designated as 106 is allowed to rise from ground to approximately one N-channel threshold, which causes the node designated 130 to rise by the same amount to a final value of two N-channel thresholds plus 100-mV. The voltage on the node designated 134 (OSCI) then starts to rise as capacitor 138 receives charge from current source P6; this action is shown in FIG. 5a. When the voltage on the OSCI line has risen to the voltage on node 130 (approximately two N-channel thresholds plus 100-mV), the BCNTL output of comparator 136 will return to its high level; and the entire process just described is then repeated.

Figure 4:
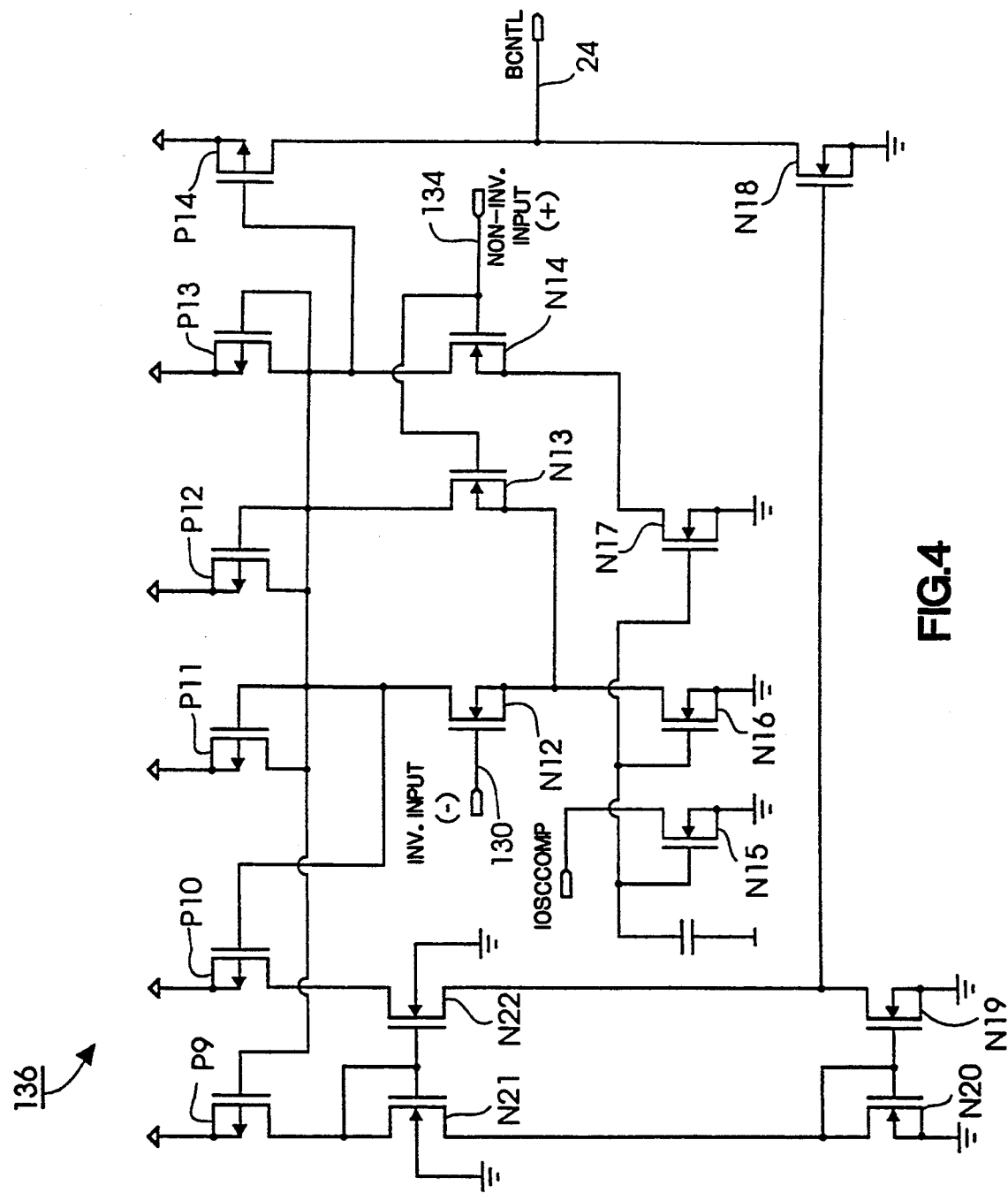
FIG. 4 is a schematic diagram of the comparator in the oscillator circuit of FIG. 3.

Turning to FIG. 4, a schematic diagram of the circuitry of comparator 136 is shown. The comparator of FIG. 4 is unique for the following reasons: (1) its differential pair loads (P11 and P12) are current sources, which are controlled by the diode-wired transistor P13. This permits large voltage output swings on the drains of transistors N12 and N13. Thus, P14 and P10 are driven with larger $V_{GS}$ values than is normally the case with conventional comparators. (2) The network formed by P9, P10, N21, N22, N20, and N19 serve to limit the current in the path formed by P10, N22, and N19—which would go to very large values of current if not limited by the fact that N22 is only capable of two times the current in N21 (all other transistors in this network are sized identically). Thus, the overall current drain of comparator of FIG. 4 is controlled while simultaneously allowing high gain and high slew rates which result from the large signal swing on the drains of transistors N12 and N13.

Figure 5B:
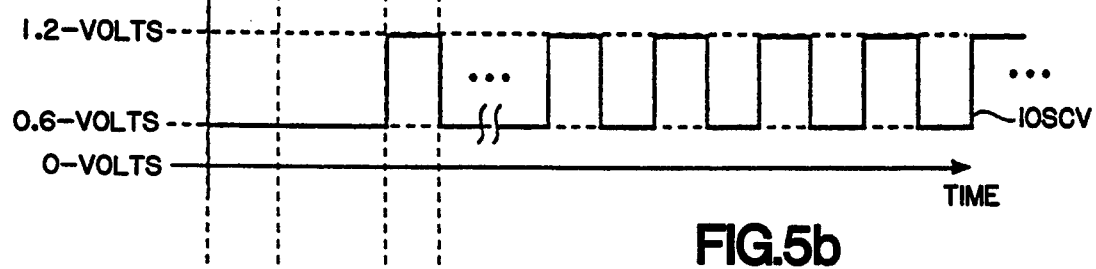
Figure 5C:
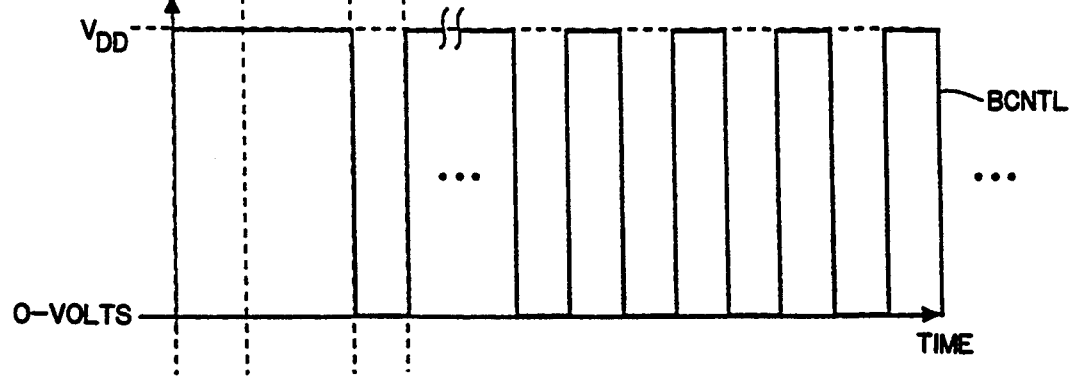

Operation of oscillator circuit 22 may be more readily appreciated with reference to the graphs of FIGS. 5a through 5c. In FIGS. 5a through 5c, certain moments in time are indicated by means of vertical dashed lines designated T12, T13, and so on. It is to be understood from the Figures that, for example, time T12 is the same for all of FIGS. 5a through 5c. In particular, it will be assumed that power is first applied to the circuitry of FIG. 3 at time T12, and that the PWRUP signal (not shown in the Figures) is asserted during the interval from T12 to T13. At time T13, the PWRUP signal falls to zero volts.

FIG. 5a is a graph of the signal OSCI from FIG. 3 that is applied to the non-inverting input of comparator 136. At time T12 the PWRUP signal goes high. At this time N11 has $V_{DD}$ on its gate and current is being drawn through it by the current source N3; thus its source (the node designated as 134—OSCI) must be approximately one N-channel threshold below $V_{DD}$. This voltage is higher than that achievable at the node designated 130 (IOSCV); thus BCNTL is forced high to $V_{DD}$ as shown in FIG. 5c. This action at BCNTL results because the gate of N13 in FIG. 4 is pulled higher than the gate of N12. Thus, the gate of P14 is pulled low, which causes BCNTL to be pulled high. FIG. 5b shows the node designated 130 (IOSCV) to be at approximately 0.6-V until T14 when OSCI falls to the same level as IOSCV—as described earlier, the voltage of IOSCV is the sum of one N-channel threshold plus approximately 100-mV when BCNTL is high and the sum of two N-channel thresholds plus approximately 100-mV when BCNTL is low.

When PWRUP goes low at time T13, BCNTL is at a high level, rendering transistors N2 and N3 conductive. Transistors N2 and N3 provide a discharge path for capacitor 138. Thus, the voltage on line 134 decays during the interval from T13 to T14. When the voltage on line 134 falls below the voltage established on line 130 (IOSCV), transistor N13 (FIG. 4) conducts less current than N12 which causes the gate of P14 to rise. This action causes P14 to conduct less current than required by N18; thus, BCNTL falls to ground.

Also during the time period from T13 to T14, the BCNTL signal on line 24 being high renders transistors N10, N7, and N8 conductive as noted above, holding the IOSCV signal on line 130 at a low level of approximately 0.6-V (the sum of N8's threshold voltage plus N7's $V_{DS}$, which is approximately 100-mV), as shown in FIG. 5b. However, when BCNTL falls to ground at time T14, transistor N10 turns off, which allows N9 to conduct; thus N9's threshold voltage is added to the sum of voltages already across N7 and N8. Therefore, line 130 rises to approximately 1.2-V when BCNTL falls to ground. Also, BCNTL's falling to ground turns off N2 and turns on P3, thus allowing capacitor 138 to begin accumulating charge through the current source formed by P6. Thus, at time T14, the OSCI signal of FIG. 5a begins to rise.

As shown in FIG. 5a, the OSCI signal rises during the interval from T14 to T15, until OSCI exceeds the voltage on line 130, which is sitting at approximately 1.2-V (the sum of voltage across transistors N8, N7, and N9). When this occurs at T15, BCNTL goes to a high level, IOSCV returns to the sum of voltage across transistors N8 and N7, and the process of discharging and charging capacitor 138 is repeated.

As noted above, it is believed that inclusion of ultraslow 10-Hz oscillator circuit 22 in the disclosed embodiment of the invention is preferable due to the savings in device size, device manufacturing cost, and power consumption it affords. For the same reasons, an implantable device in accordance with the presently disclosed embodiment of the invention also employs a floating gate electrically erasable programmable read-only memory (EEPROM) cell as a non-volatile means for storing an analog voltage.

EEPROM storage cells are well known to semiconductor circuit designers. An EEPROM cell mainly comprises a MOS transistor that stores electrical charge on an electrically isolated, conductive capacitor plate (a so-called "floating gate"). The floating gate is located above the transistor channel. The charge on the floating gate creates an electric field that modifies the conductivity of the transistor's channel. The construction and application of EEPROM storage cells would be a matter of routine to persons of ordinary skill in the field of semiconductor integrated circuit design.

The recently discovered ability of EEPROM storage cells to be operative as analog storage devices is discussed, for example, in *Electronic Design*, vol. 39, no. 2, Jan. 31, 1991, pp. 39–44; in *EDN News Edition*, vol. 36, no. 3A, Feb. 7, 1991, pp. 1 and 38; and in *ISD 1016 Series Preliminary Specifications*, January, 1991, published by Information Storage Devices, Inc. of San Jose, Calif. These references are hereby incorporated by reference in their entirety.

In the presently disclosed embodiment of the invention, an EEPROM storage cell such as is described in the above-noted references is associated with one-shot circuits 58 and 16 output, pump and recharge circuit 14 and oscillator circuit 22. For one-shots 58 and 16, the magnitude of the reference voltage stored in its associated EEPROM cell determines the one-shot's output pulse duration. An increase or decrease in the voltage stored in the associated EEPROM cell results in an increase or decrease in the duration of the one-shot's output pulse. For output, pump and recharge circuit 14, the magnitude of the reference voltage stored in its EEPROM cell determines the amplitude of the output pulse from output, pump and recharge circuit 14.

Figure 6:
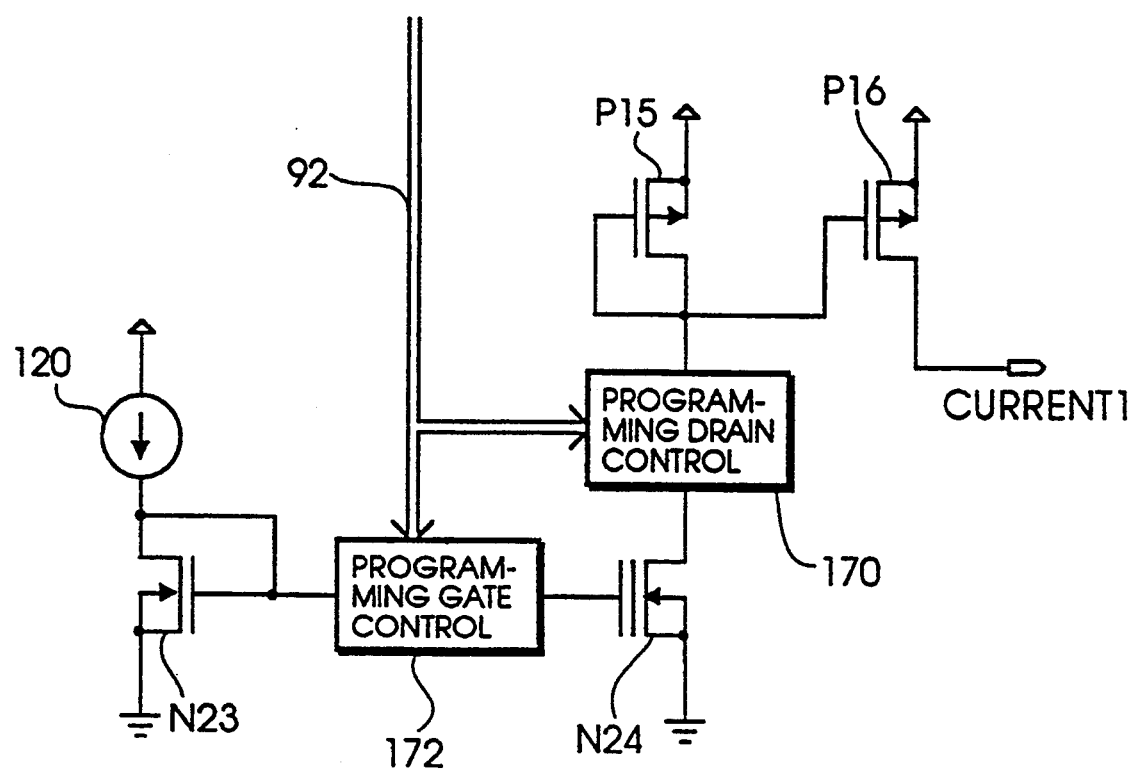
FIG. 6 is a schematic diagram of a portion of an up-down control circuit in the pacemaker of FIG. 1.

In FIG. 6, a schematic diagram of an EEPROM storage circuit 25 is shown. It is to be understood that FIG. 6 shows only one of three identical EEPROM circuits provided in up-down control circuit 90, one associated with rate one-shot 58, one associated with pulse width one-shot circuit 16 and one associated with the output, pump and recharge circuit 14. For the purposes of the following description, the EEPROM circuit 25 of FIG. 6 will be described as it operates in association with pulse width one-shot 16.

As previously described, up-down control circuit 90 provides a reference current to the P (program) input of pulse width one-shot 16 on line 96. (A reference current is also applied to the P input of rate one-shot 58 on line 94, and to the P input of output, pump, and recharge circuit 14.)

In the presently disclosed embodiment of the invention, programming drain and gate control circuits 170 and 172 utilize techniques which would be familiar to one of ordinary skill in the art of analog EEPROM programming, to either add or subtract charge on N24's floating gate (which is shown schematically as the second gate interposed between the controlled gate and the body of symbol N24). In the case of pulse width one-shot 16, the voltage stored on the floating gate of N24 determines the reference current provided on line 96 to the P input of circuit 16, which reference current in turn determines the width of output pulses generated at the O output of circuit 16, which pulses are carried on line 64 to the T (trigger) input of output, pump, and recharge circuit 14. The width of the output pulse from pulse width circuit 16 thus determines the width of pacing pulses delivered by pacemaker 10. In the case of rate one-shot 58, up-down control circuit 90 provides a reference current on line 94 based on the stored voltage on a second EEPROM cell in up-down control circuit 90 to the P input of rate one-shot 58, and this reference current determines the duration of the base pacing rate of pacemaker 10. In the case of output, pump, and recharge circuit 14, the voltage stored on the floating gate of N24 determines the reference current produced on line 98 and provided to the P input of output, pump, and recharge one-shot 14.

During programming, programming control circuits 170 and 172 establish appropriate voltages on N24's gate and drain to permit charging or discharging N24's floating gate. In particular, as shown in FIG. 6, control circuits 170 and 172 receive the logic signals 92 from circuit 78 which indicate when parameters are to be reprogrammed. In response to the logic signals 92 indicating, for example, that the pulse width should be increased, control circuits 170 and 172 vary the voltage on the floating gate of transistor N24 associated with pulse width one-shot 16. This change in voltage results in a change in the reference current CURRENT1, which in the case of the pulse width EEPROM, is conducted on line 96 to pulse width one-shot 16. If the logic signals 92 from circuit 78 call for an increase or decrease in the base pacing rate, the programming control circuits 170 and 172 associated with the pacing rate EEPROM cell will cause an increase or decrease in the voltage stored on the EEPROM cell associated with rate one-shot 58, and this increase or decrease will be reflected in a change in the reference current supplied to rate one-shot 58 on line 94.

Added charge on the floating gate of EEPROM cell N24 serves to effectively reduce the gate voltage applied to N24. During normal pacemaker operation, the net gate voltage applied to N24 is $V_g$, where $V_g$ is given by:

$$V_g = V_b + V_f$$

where $V_b$ is the voltage applied to N24's controlled gate via N23's gate-drain, and $V_f$ is the effective voltage stored on N24's floating gate. $V_f$ is a negative voltage due to the fact that electrons are stored on the floating gate.

Thus, as charge is added to the floating gate of N24, N24 is rendered less conductive than it would be if it were an ordinary N-channel MOSFET controlled by $V_b$. If N23 and N24 are biased in the sub-threshold region of operation, the equations which describe their behavior are as follows:

$$I_{ds}(N23) = J_o \times \left(\frac{w}{l}\right) \times \exp\left(\frac{(V_g - V_s - V_{thn})}{(n \times V_t)}\right)$$

$$I_{ds}(N24) = J_o \times \left(\frac{w}{l}\right) \times \exp\left(\frac{(V_g - V_s + V_f - V_{thnf})}{(b \times V_t)}\right)$$

where $J_o$ is a conduction constant determined by the process, (w/l) is the width-to-length ratio of the transistor, $V_g$ is the gate voltage, $V_s$ is the source voltage, $V_{thn}$ is the N-channel threshold voltage, $V_{thnf}$ is the EEPROM N-channel threshold voltage, $V_f$ is the effective voltage stored on N24's floating gate, n is the subthreshold conduction constant (which represents the slope of $Log(I_{ds})$ vs. $V_{gs}$ curve of the transistor in the subthreshold conduction mode), and $V_t$ is the thermal voltage (which is $k \times T/q$, where k is Boltzman's constant, T is the temperature in degrees Kelvin, and q is the charge of an electron).

Given that $I_{ds}(N23)$ is provided from current source 120 (FIG. 6), that $V_s$ is ground for both transistors, and that $V_g$ is the same for both N23 and N24, it follows that:

$$I_{ds}(N24) = I_{120} \times \exp\left(\frac{(V_f - V_{thnf} + V_{thn})}{(n \times V_t)}\right)$$

Thus, it is seen that, by adjusting the value of $V_f$ via EEPROM programming gate and drain control circuits 170 and 172, the value of $I_{ds}(N24)$ can be caused to vary.

Further reference to FIG. 6 reveals that $I_{ds}(N24)$ is applied to P15, which has its gate and drain tied together. Thus, the gate voltage on P15 is set to that voltage required to permit it to conduct current which is equal to $I_{ds}(N24)$ (i.e., $I_{ds}(P15) = I_{ds}(N24)$). P15's gate is attached to P16, therefore P16 is biased to conduct an $I_{ds}(P16)$ which is proportional to $I_{ds}(P15)$. Specifically:

$$I_{ds}(P16) = I_{ds}(P15) \times \left(\frac{S_{16}}{S_{15}}\right)$$

where $S_{16}$ is the width-to-length ratio of P16 and $S_{15}$ is the width-to-length ratio of P15. CURRENT1 in FIG. 6 is $I_{ds}(P16)$, and provides programming to pulse width one-shot 16 shown in FIG. 7.

Jumping now to FIG. 11, there is shown a prior embodiment of a bias current circuit 200 for the inventive pacemaker shown in FIG. 1. The basic bias generator 200 is formed by transistors P10, P11, N10 and N11 together with Rb. A voltage across Rb is developed as the result of the ratio of the sizes of the four transistors P10, P11, N10 and N11. The full equation for this voltage is:

$$V_r = n^{K*T/q^*}\ln((sp10/sp11)*(sn11/sn10))$$

where: n is a processing constant;

k is Boltzman's constant;

T is temperature in degrees Kelvin;

q is the charge of an electron;

sp10 is w/l of P10;

sp11 is w/l of P11;

sn10 is w/l of N10; and sn11 is w/l of N11.

N12 is sized larger than N10 by a factor K. Thus, if the source of N12 were at ground potential, it would conduct K times the current in N10. However, if N12's source voltage is raised above ground, it will conduct less current. Specifically, raising N12's source above ground reduces its $V_{gs}$. Placing R1 204 between N12's source and ground creates an IR drop across R1 204 which serves to reduce N12's Vgs and, therefore, its current. Thus, R1 204 can be sized to achieve a desired current in N12.

The current in N12 must go through P3, which is diode wired. P3's gate voltage is applied to the gates of P1 and P2. When P1 and P2 conduct, they will pass currents I1 and I2, respectively. I1 and I2 will be proportional to the ratio of their w/l to the w/l of P3 times the current in P3.

Moving now to FIG. 12, there is illustrated a preferred embodiment for a programmable bias current circuit 300 which replaces the prior art embodiment of the bias current circuit 200 shown in FIG. 11. The programmable bias current circuit 300 shown in FIG. 12 is identical to the prior art depicted in FIG. 11, except N12 is replaced with an EEPROM n-channel transistor described hereinbefore on page 27, thereby eliminating the need for a trimmable resistor 204, a capacitor 206 and a bonding pad 202. The elimination of these parts from the inventive pacemaker reduces the overall system cost, parts count and physical size. Historically, production processes were necessary to laser trim R1 204 for example, in order to achieve a desired current in N12. Furthermore, a capacitor 206 was required in the prior bias current generator circuit 200 to achieve appropriate EMI filtering and to accomplish current smoothing during periods of current switching and/or interruption. The resistor 204 and capacitor 206 in the prior bias current generator 200 were connected to the bias current generator circuit 200 by means of a bonding pad 202. Thus, as hereinbefore indicated, elimination of trim resistor 204 and capacitor 206, also result in elimination of bonding pad 202. It can therefore be seen, that elimination of resistor 204, capacitor 206 and bonding pad 202 reduce overall system cost since production processes necessary to trim resistor 204, to bond resistor 204 and capacitor 206 to pad 202, and to inspect and test the operation of bias current generator 200 with these parts is now eliminated.

Operation of the preferred embodiment of the programmable bias current generator 300 will be more readily appreciated with reference to FIG. 12. The EEPROM style transistor 302 shown in FIG. 12 consists of an electrically isolated gate (usually polysilicon) which can be charged to a negative voltage by storing electrons on this isolated gate. The net effect of this stored charge is to raise the apparent threshold voltage of the transistor 302. Thus, the gate voltage of N10 applied to the control gate of EEPROM NFG 302 (the control gate is a 2nd polysilicon gate which resides directly above and is electrically isolated from the floating gate) will cause NFG 302 to conduct a current which is predicted by:

$$I(NFG) = k*I(N10)^{exp((Vth(N10)-Vth(NFG)-Vfg)/n*Vt))}$$

where: Vth(N10) is the threshold voltage of N10;

Vth(NFG) is the threshold voltage of NFG 302 when no charge is stored on its floating gate;

Vfg is the absolute value of the negative voltage stored on NFG's 302 floating gate;

n is a processing constant; and

Vt is k*T/q, which is defined above, is thermal voltage. This expression for I(NFG) assumes NFG 302 is in subthreshold conduction; thus the current is an exponential function of voltage. In the prior art bias current generator 200 as well as in the preferred embodiment for the programmable bias current generator 300, the only transistors which must be in subthreshold conduction are P10 and P11. All others may be in either subthreshold or strong inversion. In strong inversion, the currents bear a square law relationship to Vgs rather than an exponential relationship. It is noteworthy that the accuracy of the current mirrors formed by N10, N11 and N12 (or NFG) and P3, P1 and P2 is improved by their being in strong inversion, because the square law relationship is not as sensitive to small changes in threshold voltage.

Figure 13A:
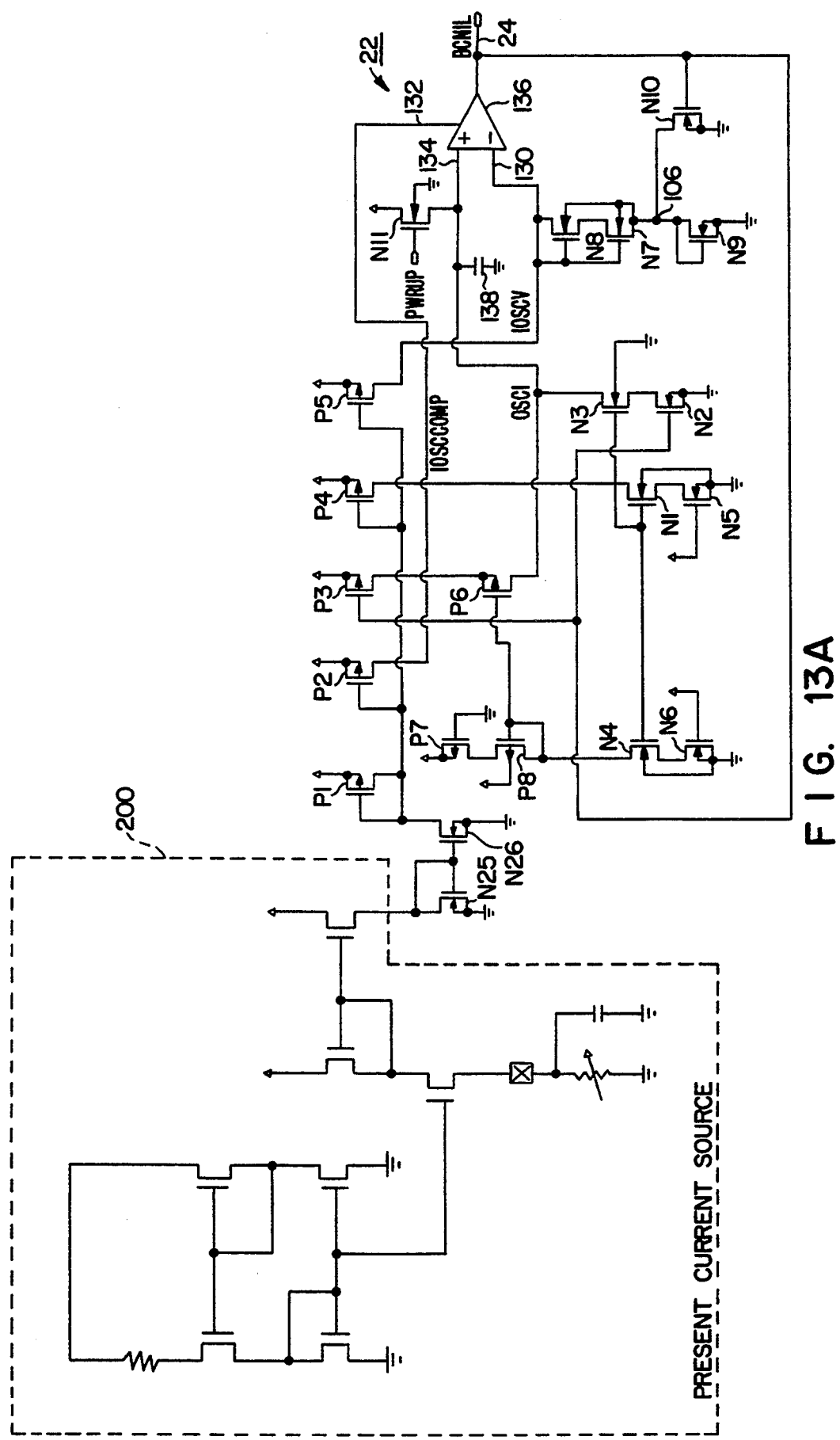
FIG. 13A is a schematic diagram illustrating the prior art bias current circuit of FIG. 11 coupled to the oscillator circuit shown in FIG. 3.

Moving now to FIG. 13A, it can be seen that the prior bias current generator 200 which had been used in previous pacemakers to power the oscillator circuit 22, required extra components hereinbefore discussed, namely a trim resistor 204, a capacitor 206 and a bonding pad. These components are eliminated in the present inventive pacemaker which uses the programmable bias current generator 300 depicted in FIG. 13B.

Figure 13B:
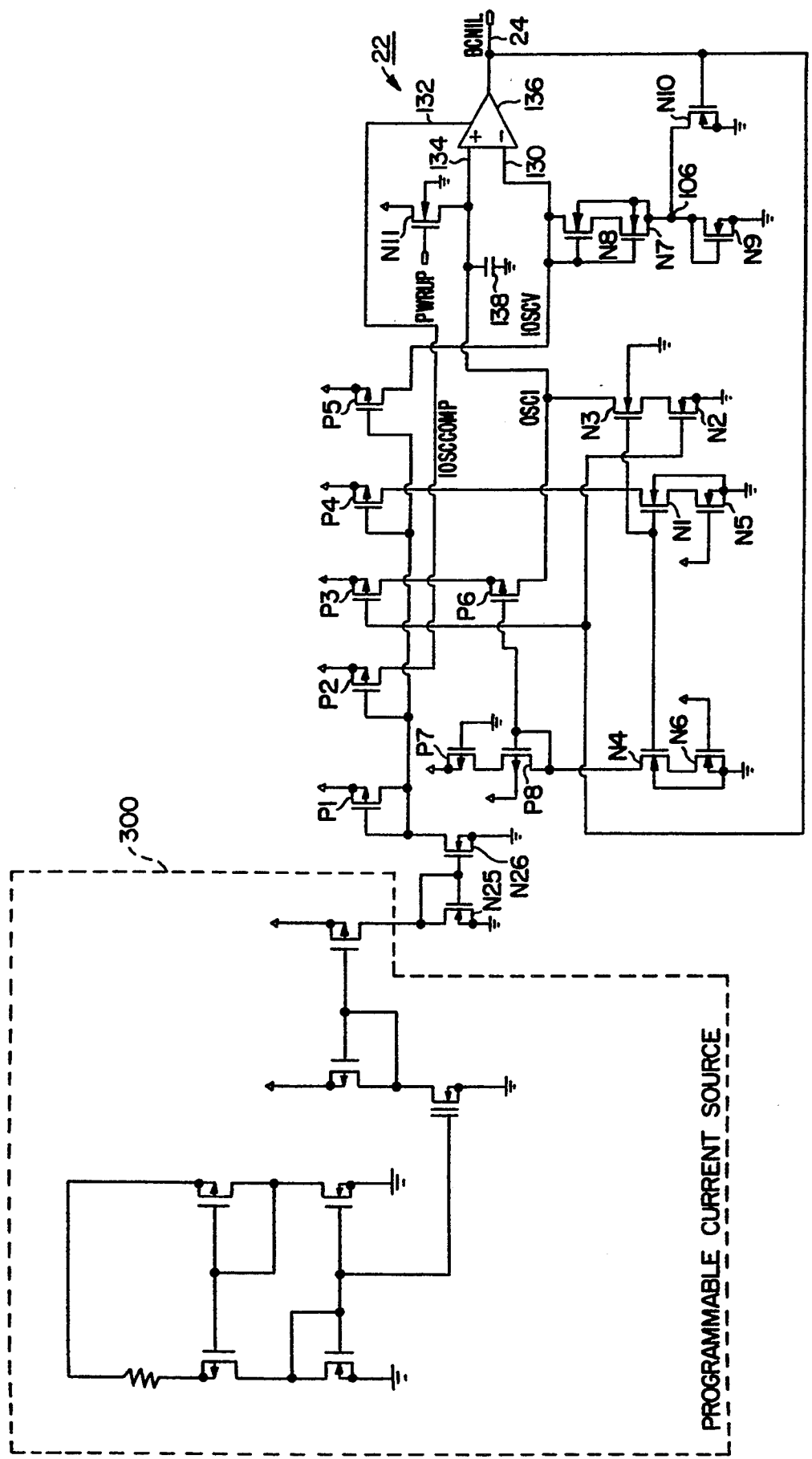
FIG. 13B is a schematic diagram illustrating the programmable bias current circuit of FIG. 12 coupled to the oscillator circuit shown in FIG. 3.
Figure 14:
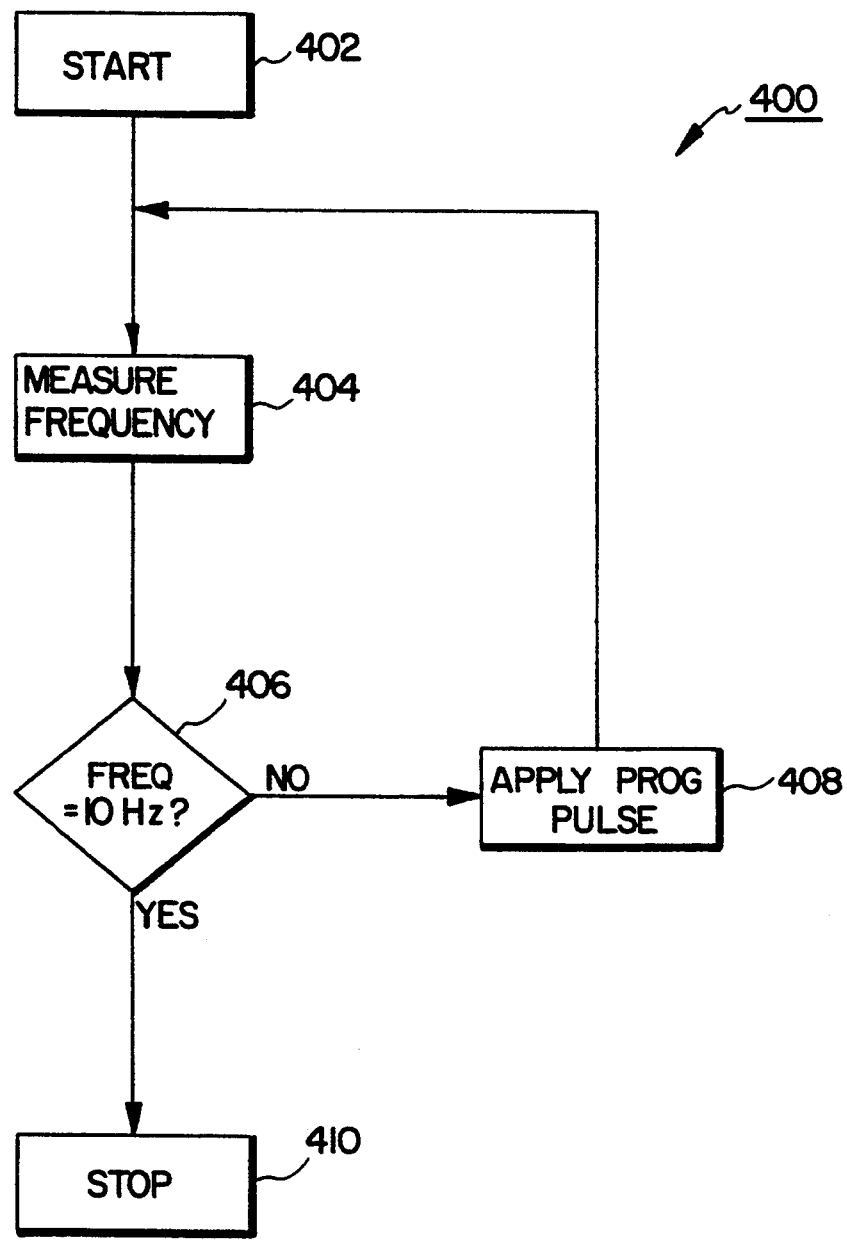
FIG. 14 is a flow diagram illustrating how the circuit depicted in FIG. 13B is used to program the oscillator circuit shown in FIG. 3.

In the preferred embodiment illustrated in FIGS. 12 and 13B, programmable bias current generator 300 is programmed during the manufacturing process utilizing techniques familiar to one of ordinary skill in the art of analog EEPROM programming, to either add or subtract charge on the floating gate of EEPROM NFG 302. Thus, it is not necessary that programmable bias current generator 300 permanently employ drain and gate control circuits such as those described hereinbefore for the EEPROM storage circuit 25 illustrated in FIG. 6. At IC wafer probe, for example, the floating gate transistor 302 of FIG. 12 is programmed via a standard probe pad (not shown) with 9-18 volt positive pulses via circuitry on a wafer probe card (not shown). A programming pulse is applied changing the threshold of transistor 302, modifying the current output I1 for example. This programmed current changes the frequency of the 10 Hz oscillator 22 of FIG. 3. As shown in FIG. 14, by alternately programming the current via a programming pulse application 408 and measuring the output frequency 404, the 10 Hz oscillator 22 is nonvolatiley trimmed to a predetermined value. Subsequent manufacturing steps i.e., wafer scribe and break, packaging, burn-in, assembly into hybrids and implantable medical devices, do not affect this preprogrammed trim. Significant cost reduction, reduced size and improved reliability result by elimination of components and subsequent tests and trims.

Figure 15:
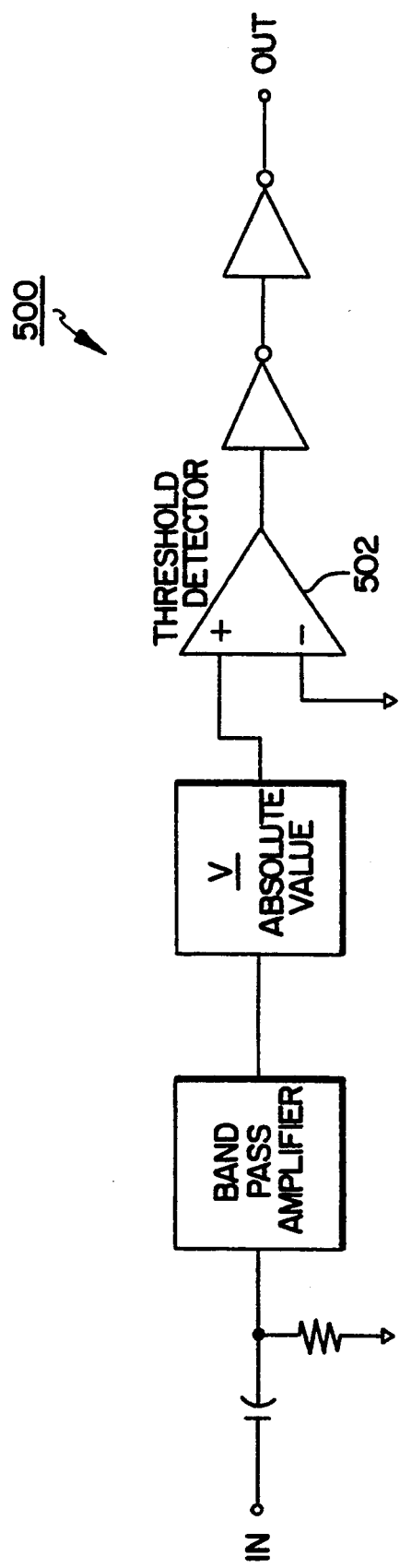
FIG. 15 is a partially block diagram illustrating a voltage sensitive circuit which utilizes a voltage threshold detector to sense voltage level changes for a varying input voltage, in which the threshold detector may be implemented with one embodiment of the present invention as shown in FIG. 17.
Figure 16:
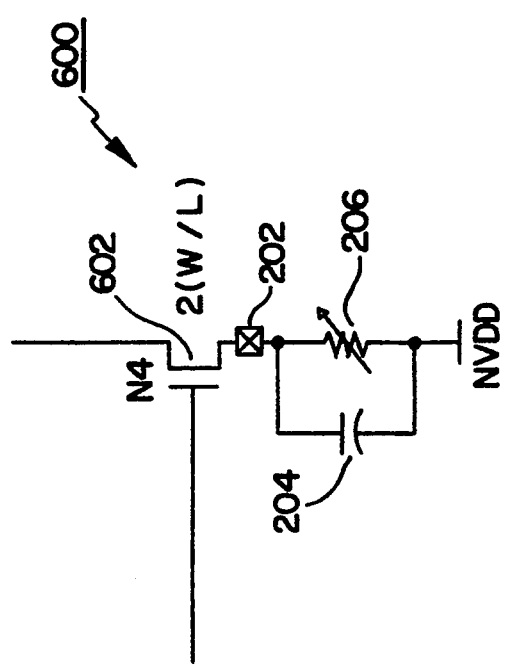
FIG. 16 illustrates an existing implementation of a portion of a prior embodiment of a bias current circuit shown in FIG. 11.
Figure 17:
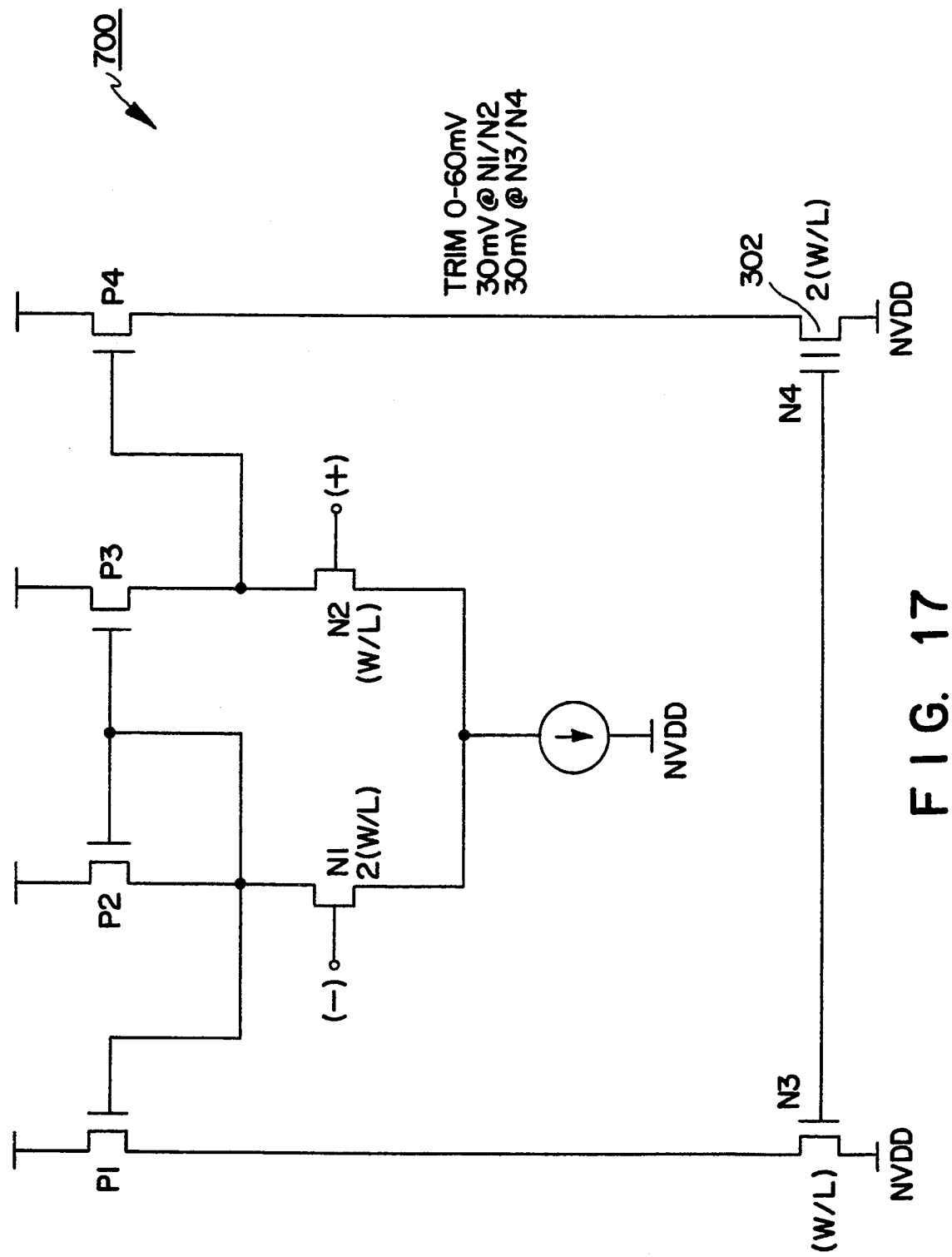
FIG. 17 is a schematic diagram illustrating conversion of the bias current circuit depicted in FIG. 16 to a programmable voltage sensitive circuit useful as a voltage threshold detector.

FIG. 15 illustrates a voltage sensitive circuit 500 which utilizes a a voltage threshold detector 502 to sense voltage level changes for a varying input voltage. One preferred embodiment 700 for threshold detector 502 is illustrated in FIG. 17. In FIG. 17, a floating gate transistor 302 replaces the prior art components depicted in FIG. 16, namely capacitor 204, resistor 206, and bonding pad 202. The advantages offered by incorporation of transistor 302 are identical to those discussed hereinbefore at pages 35-37 for programmable bias current circuit 300.

Figure 7:
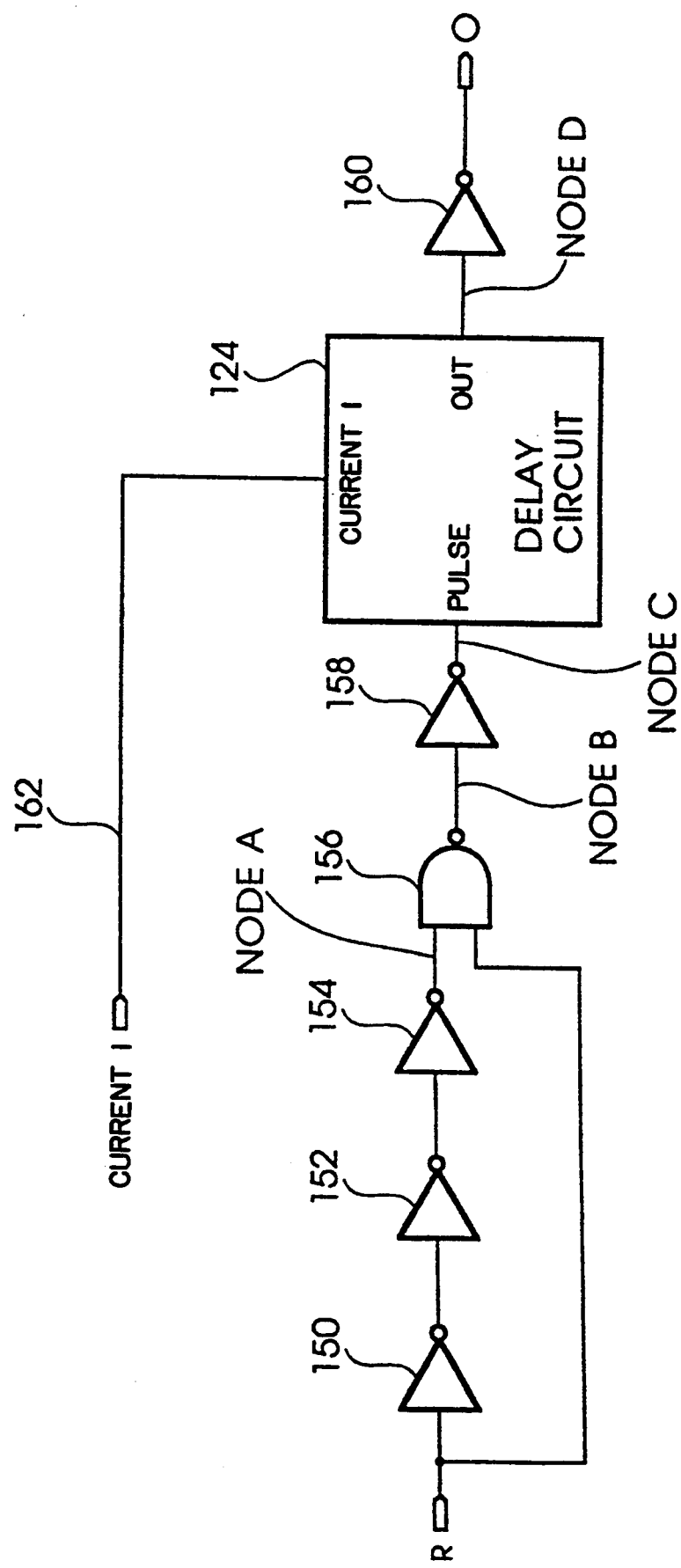
FIG. 7 is a block diagram of a one-shot pulse-generating circuit in the pacemaker of FIG. 1.
Figure 8:
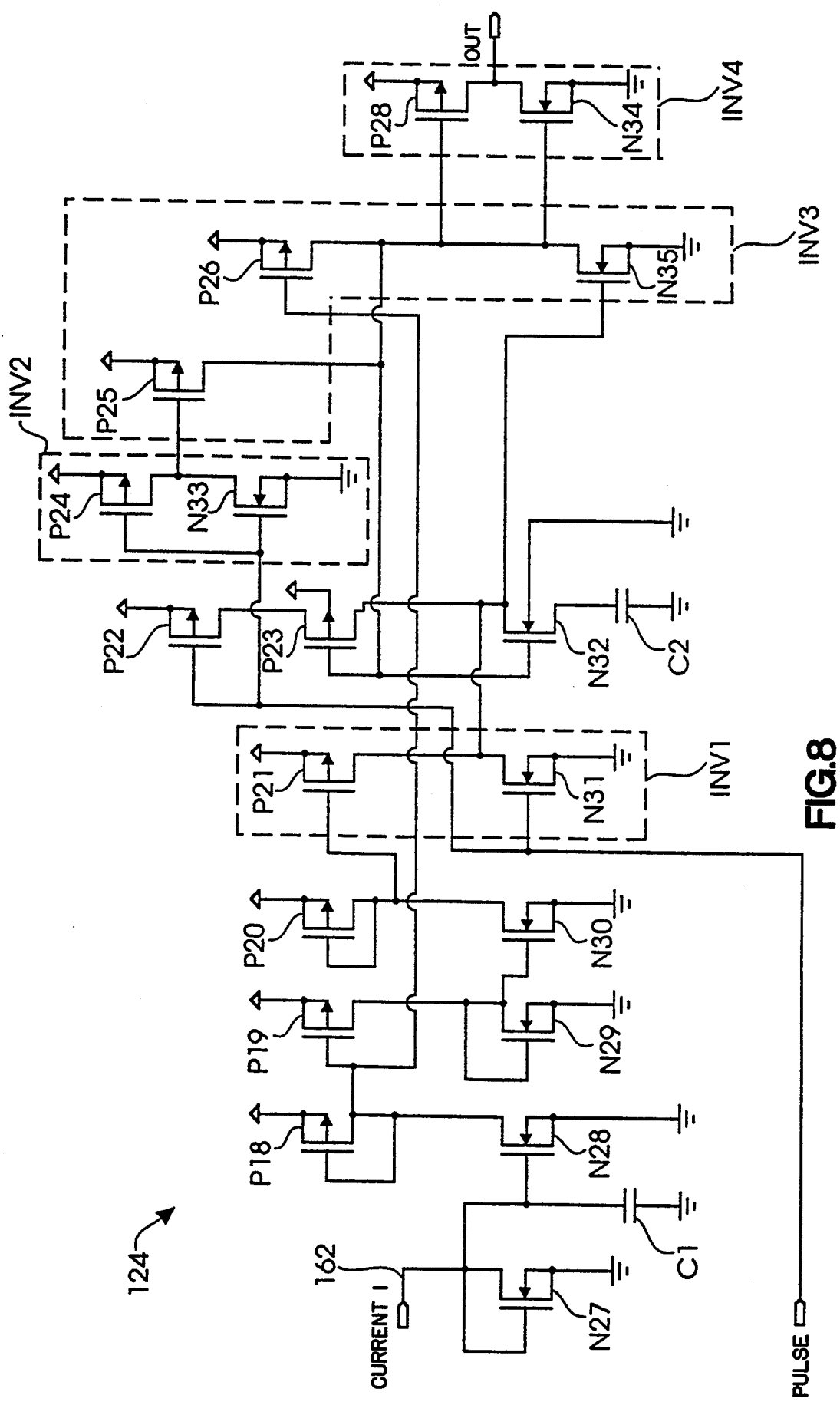
FIG. 8 is a schematic diagram of the delay element circuit of FIG. 7.

In FIG. 7, the current-controlled signal CURRENT1 produced by the circuitry of FIG. 6 on line 162 is shown being applied to the CURRENT1 input of a one-shot circuit 124. A schematic diagram of one implementation of one-shot circuit 124 is shown in FIG. 8. Recall from FIG. 6 that the current level of the CURRENT1 signal corresponds to the amount of charged programmed on to the floating gate of EEPROM cell N24. Also, recall from FIG. 1 that the "T" input of output, pump and recharge circuit 14 receives the output pulse from pulse width one-shot 16. The pulse applied to the "T" input of output and pump circuit 14 in FIG. 1 has a duration corresponding to the desired width of a pacing pulse to be delivered via capacitor 66 to the patient's heart.

FIG. 7 represents the presently preferred implementation of a circuit which is duplicated in pulse width one-shot circuit 16, rate one-shot and TMT circuit 58, and the recharge one-shot portion of output circuit 14. The circuit of FIG. 7 consists of inverters 150, 152, 154, 158, and 160, a NAND gate 156, and a delay circuit 124, which receives a programmed current from up-down control circuit 90 (in the case of pulse width one-shot 16 and rate one-shot 58) or a fixed current (in the case of recharge one-shot in circuit 14), on CURRENT1 line 162. Delay circuit 124 is triggered by a signal at its PULSE input (node C).

Figure 9:
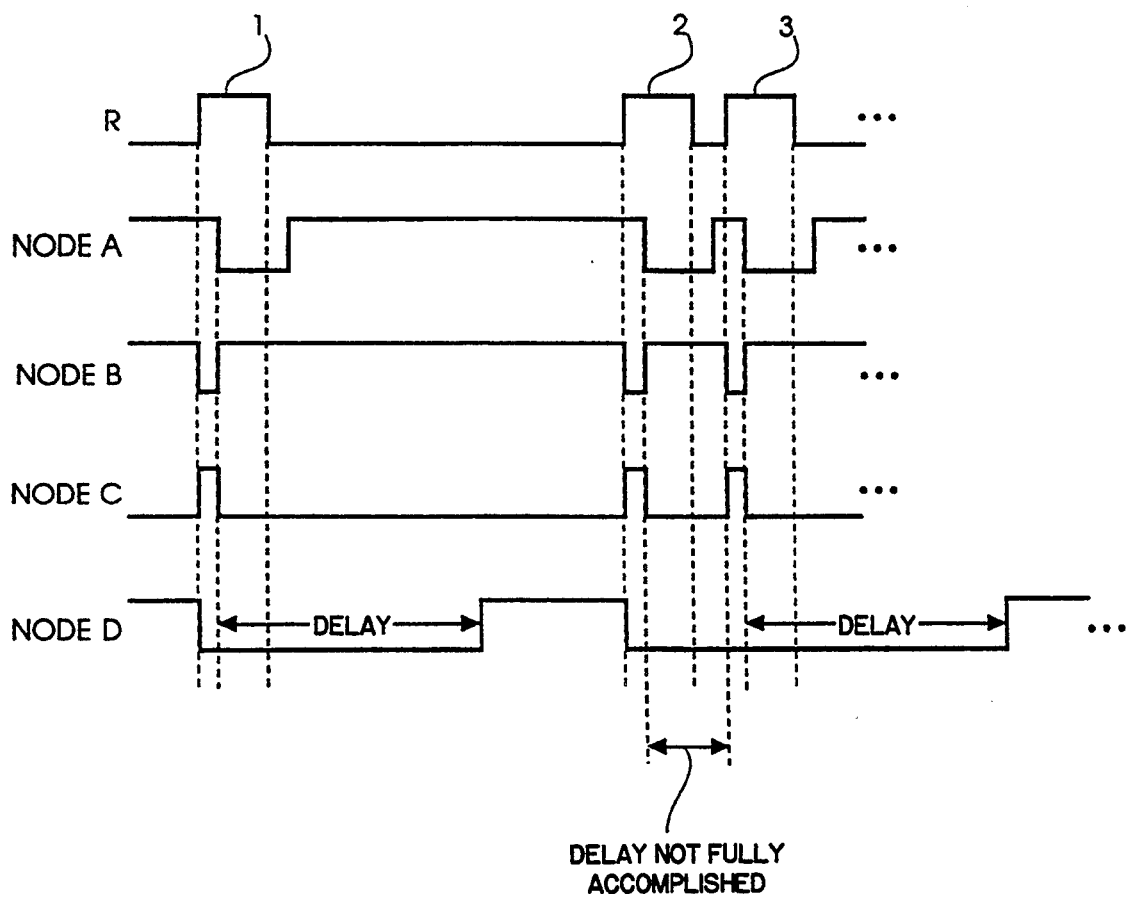
FIG. 9 is a timing diagram of the one-shot pulse generating circuit of FIGS. 6 through 8.

Delay circuit 124, shown in FIG. 8, is the controlling timing element; its delay is established by the reference current on CURRENT1 line 162 applied to its CURRENT1 input. The waveforms shown in the timing diagram of FIG. 9 reveal the operation of this circuit. Inverters 150, 152, and 154 which drive node A in FIG. 7 and NAND gate 156 create a narrow pulse at node B which occurs at the leading edge of the signal applied to the R input and lasts only as long as the propagation delay through inverters 150, 152, and 154. The signal at node C is the logical inversion of that at node B, and drives the PULSE input of delay circuit 124. The output signal from the OUT output of circuit 124 is forced low when the R delay circuit input is high; as soon as the signal at the R input goes low, the time delay starts. Unless interrupted by another rising edge of the signal applied at the R input, node D (the output of Delay element 124) will go high at the end of the time delay. Thus, it can be seen that the O output (i.e., line 64 in FIG. 1) of the pulse width one-shot goes high at the leading edge of R and goes low approximately one time delay later. However, if an R leading edge occurs before this time delay is completed, the time delay is reset, leaving the O output signal at a logical high level. The 0 output will remain high until the absence of R leading edges permits the time delay to be completed.

Reference to FIG. 8 will now permit a description of how delay element 124 functions and how the reference CURRENT1 controls the time delay. CURRENT1 is applied to the gate and drain of N27, which sets up the voltage required to allow N27 to carry this current. N27 and N28 have the same width-to-length ratio; therefore, N28's $I_{ds}$ will equal CURRENT1. Capacitor C1, which is preferably a 3-pF capacitor, provides noise and power supply rejection. N28's $I_{ds}$ is applied to P18's gate and drain, which sets up the voltage required to carry this current. Thus, P19 and P26 are driven to carry this amount of current in proportion to the ratio of their respective width-to-length ratio to P18's width-to-length ratio. P18, P19, N29, N30, P20, and P21 form a cascade of current mirrors/sources, in which the ratio of the width-to-length ratios is decreased to permit P21's $I_{ds}$ to be 0.01 times P18's $I_{ds}$, or 1.5-nA nominally. Thus, circuit 124 comprises: (1) an inverter INV1 formed by current source P21 and N31; (2) an inverter INV2 formed by P24 and N33; (3) an inverter INV3 formed by P25, current source P26, and N35; (4) an inverter INV4 formed by P28 and N34; (5) P22 and P23, which provide a path for rapidly pulling N35's gate to the positive power supply; and (6) N32 and C2.

The basic operation of delay element 124 is as follows: When the PULSE input signal to circuit 124 is held high, (1) N31 pulls N35's gate to ground; (2) P22 is off; (3) INV2's output goes low; (4) P25 is on and pulls INV3's output high; (5) P23 is off and N32 is on; (6) C2 is discharged to ground via N31; and (7) OUT is low. This state is achieved immediately upon application of a high PULSE input voltage. When PULSE goes low, delay circuit 124 goes through three states—(1) charge, (2) transition, and (3) stable output. When PULSE first goes low, (1) N31 is off; (2) P22 is on; (3) INV2's output is high; (4) P25 is off; (5) INV3's output is still high; (6) INV4's output is still low; (7) N32 is on; and (8) C2 begins to be charged toward the positive supply by current source P21—this is the charging state. The charging state will continue until C2 and N35's gate (which are tied together until N32 is turned off) reach, approximately, the threshold voltage of N35—at which time N35 will begin to conduct. The transition state begins when N35 begins to conduct. As its gate voltage continues to rise, N35 will eventually be able to conduct more current than that supplied by current source P26; at that time INV3's output will start to fall downward toward ground. As INV3's output falls lower than P23's threshold voltage below the positive supply, P23 becomes conductive, which then accelerates the charging of C2 and N35's gate past N35's threshold voltage. At this point, the fall of INV4's output toward ground accelerates, which leads to N32 becoming increasingly resistive, which allows N35's gate to be charged even more rapidly toward the positive supply. The net result is that N35's gate charges to the positive supply very rapidly once N35's threshold voltage is reached, which causes INV3's output to go low and INV4's output to go high—at this point the delay element is in its stable output state.

The actual delay of the delay element is the sum of the delay element's charge time plus transition time. By design, the transition time is a small fraction of the charge time. Therefore, for practical purposes, the delay time may be expressed as:

$$\text{Delay} = C2 \times \left(\frac{V_{thn}}{I}\right)$$

where $V_{thn}$ is the N-channel threshold voltage, I is the current of current source P21 (i.e., 1.5-nA), and C2 is 1.06-pF.

As previously noted, a separate delay circuit 124 such as is shown in FIG. 8 is provided rate one-shot and TMT circuit 58, in pulse width one-shot 16, and output, pump, and recharge circuit 14. Circuit 58 operates identically to circuit 14. When its input, R, goes high, its output, O, goes high and remains high for the time established by the current supplied by circuit 90. This current from circuit 90 on line 94 is generated in the same way as that described for CURRENT1 above. C2's value, however, is 2,000-pF, giving a nominal rate one-shot interval of 923-mSec, or 65-PPM.

Delay circuit 124 is also duplicated in a 5-mSec recharge one-shot in output circuit 14. In this case, the circuit functions identically as the pulse width one-shot described above, with the exception that C2 has a value of 10-pF and the current control of FIG. 6 is modified by replacing N24 with a standard N-channel CMOS transistor (i.e., non-EEPROM). Thus, a fixed, non-programmable current of 150-nA is used.

Figure 10:
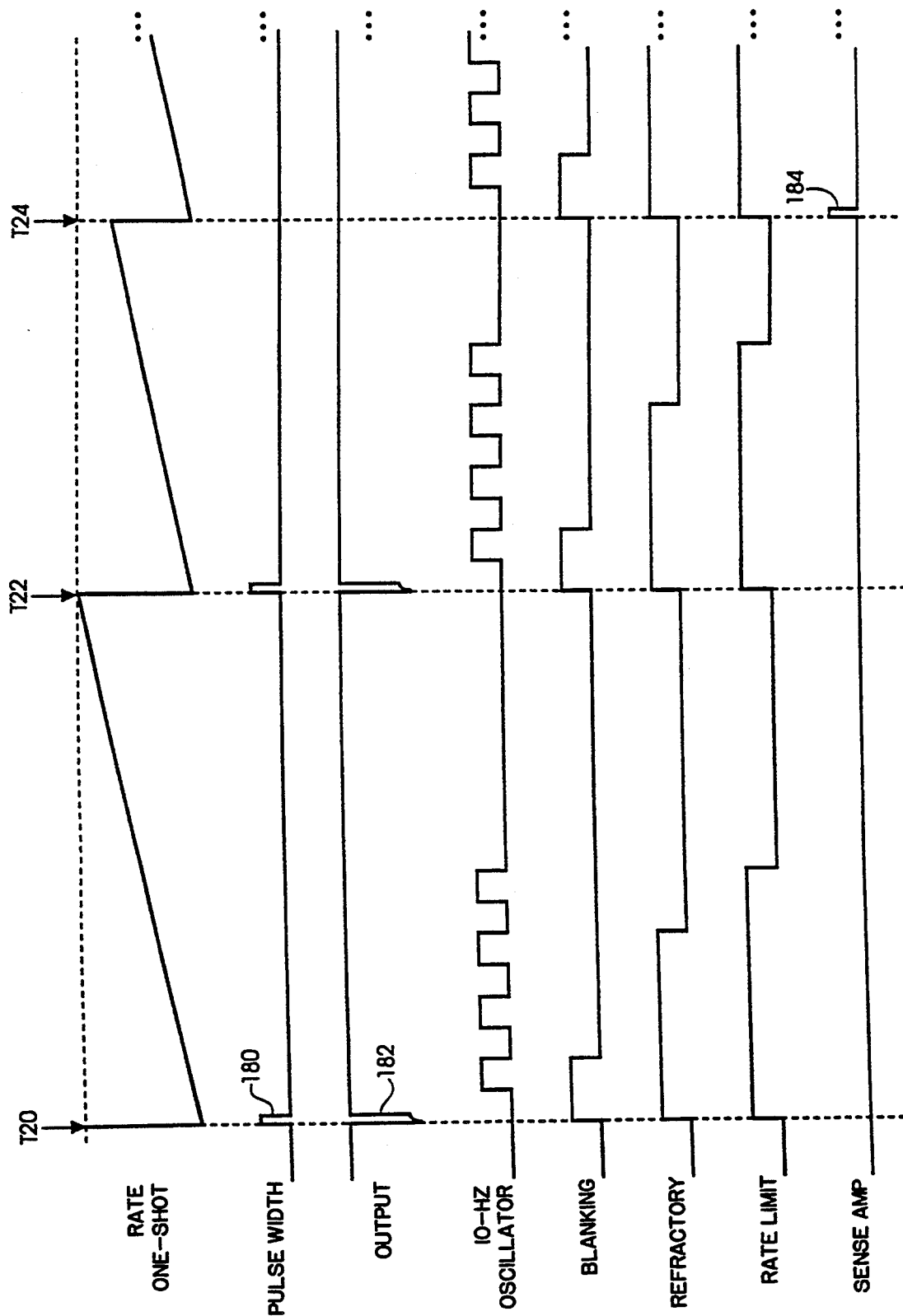
FIG. 10 is a timing diagram of the pacemaker circuit of FIG. 1.

Pacing operation of pacemaker 10 from FIG. 1 may be better appreciated with reference to the timing diagram of FIG. 10. The events depicted in FIG. 10 begin at time T20 with the delivery of a pacing pulse. The waveform labeled RATE ONE SHOT in FIG. 10 depicts the charge on capacitor C2 in the delay circuit 124 associated with rate one-shot 58. At time T20, the capacitor quickly discharged and immediately begins the charging cycle which defines the delay of delay circuit 24, with the rate of charging being determined by the reference current applied at the CURRENT1 input to circuit 124. The delivery of a pacing pulse occurs in response to the generation of an output pulse from the O output of pulse width one-shot 16; this signal is labeled PULSE WIDTH in FIG. 10. At time T20, pulse width one-shot 16 produces an output pulse designated 180 in FIG. 10, the duration of which is determined by the reference current applied to the CURRENT1 input to the delay circuit 124 associated with pulse width one-shot 16. Pulse 180 is applied to the T (trigger) input to output, pump, and recharge circuit 14, causing circuit 14 to produce an output pulse 182 at from its O output to output capacitor 66.

As previously described with reference to FIG. 1, 10-hz oscillator circuit 22, rate limit circuit 26, blanking circuit 28, and refractory circuit 30 are also restarted upon delivery of a pacing pulse. Blanking circuit asserts its BLANKING output signal on line 29, as shown in FIG. 10, for 100-mSec, i.e., for one 10-hz clock cycle. Refractory circuit 30 asserts its REFRACTORY output signal on line 44 for 300-mSec, i.e., for three 10-hz clock cycles. Similarly, rate limit circuit 26 asserts its RATE LIMIT output on lines 40 and 62 for 400-mSec, i.e., for four 10-hz clock cycles.

With continued reference to FIG. 10, between times T20 and T22, no intrinsic cardiac event was sensed, and therefore capacitor C2 in rate one-shot circuit 58 is allowed to complete another charging cycle, reaching its maximum value at time T22 and immediately discharging. Expiration of the rate one-shot causes 10-hz oscillator 22, rate limit circuit 26, blanking circuit 28, and refractory circuit 30 to be restarted, and causes pulse width one-shot 16 and output, pump, and recharge circuit 14 to deliver a pacing pulse.

At time T24, before rate one-shot 58 has had time to complete the C2 capacitor charging cycle, a sensed event occurs causing sense amplifier 20 to produce a SENSE AMP pulse 184 on line 21. As previously described with reference to FIG. 1, sense amp pulse 184 is propagated through D flip-flop 46, and AND gate 82 to cause rate one-shot 58 to discharge capacitor C2 and restart the capacitor charging cycle.

From the foregoing detailed description of a specific embodiment of the present invention, it should be apparent that a simple, limited-function implantable medical device has been disclosed. The disclosed device makes use of several subsystems which minimize the size and cost of the device, reduce the size and number of components, while maximizing its efficiency of operation and simplicity of design. While a particular embodiment of the invention has been disclosed herein in detail, this has been done for the purposes of illustration only, and is not intended to limit the scope of the invention as defined in the claims which follow. It is to be understood that various substitutions, alterations, or modifications can be made to the disclosed embodiment without departing from the spirit and scope of the claims.

For example, although the present invention has been described in the context of a cardiac pacemaker, it is believed by the inventors that the present invention may be advantageously practiced in the context of other medical devices, such as cardioverters, defibrillators, neural stimulators, or other implantable devices having synchronously operated or non-invasively programmable components. In addition, while particular implementations (including specifications of semiconductor device sizes and types) of certain pacemaker subsystems have been described above, it is to be understood that these are simply the implementations presently preferred or contemplated by the inventors, and are not to be taken as limiting the present invention to the disclosed embodiments.

What is claimed is:

1. A method of adjusting an operating parameter in an implantable cardiac pacemaker, said pacemaker having at least one transistor having a floating gate, wherein voltage on said floating gate controls said operating parameter, said method comprising the following ordered steps:
   a. activating said implantable cardiac pacemaker;
   b. measuring said operating parameter;
   c. determining if said operating parameter is less than a predetermined value;
   d. applying a programming pulse to the floating gate of said transistor to increase said operating parameter if said operating parameter is less than said predetermined value;
   e. measuring said operating parameter after said application of said programming pulse; and
   f. repeating steps c through e continuously until said operating parameter is at least equal to said predetermined value.

2. The method of claim 1 wherein said operating parameter is pacing rate and wherein said step of applying a programming pulse comprises applying said programming pulse to increase pacing rate.

3. The method of claim 1 wherein said operating parameter is pacing pulse width and wherein said step of applying a programming pulse comprises applying said programming pulse to increase pacing pulse width.

4. The method of claim 1 wherein said operating parameter is pacing pulse amplitude and wherein said step of applying a programming pulse comprises applying said programming pulse to increase pacing pulse amplitude.

5. A method of adjusting an operating parameter in an implantable cardiac pacemaker, said pacemaker containing at least one transistor having a floating gate, wherein voltage on said floating gate controls said operating parameter, said method comprising the following ordered steps:
   a. activating said implantable cardiac pacemaker;
   b. measuring said operating parameter;
   c. determining if said operating parameter is greater than a predetermined value;
   d. applying a programming pulse to the floating gate of said transistor to decrease said operating parameter if said operating parameter is greater than said predetermined value;
   e. measuring said operating parameter after said application of said programming pulse; and
   f. repeating steps c through e continuously until said operating parameter is no greater than said predetermined value.

6. The method of claim 1 or claim 5 wherein said step of applying a programming pulse comprises applying a pulse of about 9 volts to about 18 volts.

7. The method of claim 5 wherein said operating parameter is pacing rate and wherein said step of applying a programming pulse comprises applying said programming pulse to decrease pacing rate.

8. The method of claim 5 wherein said operating parameter is pacing pulse width and wherein said step of applying a programming pulse comprises applying said programming pulse to decrease pacing pulse width.

9. The method of claim 5 wherein said operating parameter is pacing pulse amplitude and wherein said step of applying a programming pulse comprises applying said programming pulse to decrease pacing pulse amplitude.

10. A method of adjusting an operating parameter in an implantable stimulator circuit, said implantable stimulator circuit having at least one transistor having a floating gate, wherein voltage on said floating gate controls said operating parameter, said method comprising the following ordered steps:
    a. activating said implantable stimulator circuit;
    b. measuring said operating parameter;
    c. determining if said operating parameter is less than a predetermined value;
    d. applying a programming pulse to the floating gate of said transistor to increase said operating parameter if said operating parameter is less than said predetermined value;
    e. measuring said operating parameter after said application of said programming pulse; and
    f. repeating steps c through e continuously until said operating parameter is at least equal to said predetermined value.

11. The method of claim 10 wherein said operating parameter is a bias current and wherein said step of applying a programming pulse comprises applying said programming pulse to increase said bias current.

12. The method of claim 10 wherein said operating parameter is a reference voltage and wherein said step of applying a programming pulse comprises applying said programming pulse to increase said reference voltage.

13. The method of claim 10 wherein said operating parameter is a detector threshold and wherein said step of applying a programming pulse comprises applying said programming pulse to increase said detector threshold.

14. The method of claim 10 wherein said operating parameter is a battery monitor threshold and wherein said step of applying a programming pulse comprises applying said programming pulse to increase said battery monitor threshold.

15. The method of claim 10 wherein said operating parameter is an oscillator frequency and wherein said step of applying a programming pulse comprises applying said programming pulse to increase said oscillator frequency.

16. The method of claim 10 wherein said operating parameter is a one-shot period and wherein said step of applying a programming pulse comprises applying said programming pulse to increase said one-shot period.

17. A method of adjusting an operating parameter in an implantable stimulator circuit, said implantable stimulator circuit containing at least one transistor having a floating gate, wherein voltage on said floating gate controls said operating parameter, said method comprising the following ordered steps:
    a. activating said implantable stimulator circuit;
    b. measuring said operating parameter;

c. determining if said operating parameter is greater than a predetermined value;

d. applying a programming pulse to the floating gate of said transistor to decrease said operating parameter if said operating parameter is greater than said predetermined value;

e. measuring said operating parameter after said application of said programming pulse; and f. repeating steps c through e continuously until said operating parameter is no greater than said predetermined value.

18. The method of claim 10 or claim 17 wherein said step of applying a programming pulse comprises applying a pulse of about 9 volts to about 18 volts.

19. The method of claim 17 wherein said operating parameter is a bias current and wherein said step of applying a programming pulse comprises applying said programming pulse to decrease said bias current.

20. The method of claim 17 wherein said operating parameter is a reference voltage and wherein said step of applying a programming pulse comprises applying said programming pulse to decrease said reference voltage.

21. The method of claim 17 wherein said operating parameter is a detector threshold and wherein said step of applying a programming pulse comprises applying said programming pulse to decrease said detector threshold.

22. The method of claim 17 wherein said operating parameter is a battery monitor threshold and wherein said step of applying a programming pulse comprises applying said programming pulse to decrease said battery monitor threshold.

23. The method of claim 17 wherein said operating parameter is an oscillator frequency and wherein said step of applying a programming pulse comprises applying said programming pulse to decrease said oscillator frequency.

24. The method of claim 17 wherein said operating parameter is a one-shot period and wherein said step of applying a programming pulse comprises applying said programming pulse to increase said one-shot period.

* * * * *

UNITED STATES PATENT AND TRADEMARK OFFICE
CERTIFICATE OF CORRECTION

PATENT NO. : 5,391,188

DATED : Feb. 21, 1995

INVENTOR(S) : Gary E. Nelson et al.

Page 1 of 2

It is certified that error appears in the above-indentified patent and that said Letters Patent is hereby corrected as shown below:

Column 6, line 23, delete "Mealtronic", and insert in its stead --Medtronic--.

Column 6, line 40, delete "Mealtrronic", and insert in its stead --Medtronic--.

Column 6, line 55, delete "these." and insert in its stead --these--.

Column 20, line 52, delete $$I_{ds}(N24) = J_o \times \left(\frac{w}{l}\right) \times \exp\left(\frac{(V_g - V_s + V_f - V_{thnf})}{(b \times V_t)}\right)$$

UNITED STATES PATENT AND TRADEMARK OFFICE
CERTIFICATE OF CORRECTION

PATENT NO. : 5,391,188  
DATED : Feb. 21, 1995  
INVENTOR(S) : Gary E. Nelson et al.

Page 2 of 2

It is certified that error appears in the above-indentified patent and that said Letters Patent is hereby corrected as shown below:

and insert instead $$I_{ds}(N24) = J_o \times \left(\frac{w}{l}\right) \times \exp\left(\frac{(V_g - V_s + V_f - V_{thnf})}{(n \times V_t)}\right)$$

Signed and Sealed this

Nineteenth Day of September, 1995

Attest:

BRUCE LEHMAN

*Attesting Officer*   *Commissioner of Patents and Trademarks*